US009430825B2

(12) United States Patent
Iwase et al.

(10) Patent No.: US 9,430,825 B2
(45) Date of Patent: Aug. 30, 2016

(54) IMAGE PROCESSING APPARATUS, CONTROL METHOD, AND COMPUTER READABLE STORAGE MEDIUM FOR ANALYZING RETINA LAYERS OF AN EYE

(75) Inventors: Yoshihiko Iwase, Yokohama (JP); Hiroshi Imamura, Tokyo (JP); Daisuke Furukawa, Koganei (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 880 days.

(21) Appl. No.: 13/322,905

(22) PCT Filed: May 13, 2010

(86) PCT No.: PCT/JP2010/058490
§ 371 (c)(1),
(2), (4) Date: Nov. 28, 2011

(87) PCT Pub. No.: WO2010/140476
PCT Pub. Date: Dec. 9, 2010

(65) Prior Publication Data
US 2012/0070049 A1    Mar. 22, 2012

(30) Foreign Application Priority Data

Jun. 2, 2009    (JP) .................................. 2009-133454

(51) Int. Cl.
*G06K 9/00*    (2006.01)
*G06T 7/00*    (2006.01)
(Continued)

(52) U.S. Cl.
CPC ........... *G06T 7/0012* (2013.01); *G06T 7/0083* (2013.01); *G06T 7/602* (2013.01); *G01N 21/4795* (2013.01); *G06T 2207/10101* (2013.01); *G06T 2207/30041* (2013.01)

(58) Field of Classification Search
CPC .................. G06T 7/0012; G06T 2207/10101; G06T 2207/30041
See application file for complete search history.

(56) References Cited

U.S. PATENT DOCUMENTS

| 2008/0100612 A1* | 5/2008 | Dastmalchi et al. ......... 345/418 |
| 2009/0268159 A1* | 10/2009 | Xu et al. ...................... 351/206 |
| 2010/0220914 A1* | 9/2010 | Iwase ................... A61B 5/0066 382/131 |

FOREIGN PATENT DOCUMENTS

| EP | 2189110 A1 * | 5/2010 |
| JP | 2007-325831 A | 12/2007 |

(Continued)

OTHER PUBLICATIONS

Machine Translation of JP 2009-061203.*
(Continued)

*Primary Examiner* — Stephen R Koziol
*Assistant Examiner* — Timothy Choi
(74) *Attorney, Agent, or Firm* — Carter, DeLuca, Farrell & Schmidt, LLP

(57) ABSTRACT

An image processing apparatus, which analyzes retina layers of an eye to be examined, comprising, means for extracting a feature amount, which represents an anatomical feature in the eye to be examined, from a projection image obtained from a tomogram of the retina layers and a fundus image of the eye to be examined, means for determining a type of the anatomical feature based on the feature amount, means for deciding layers to be detected from the retina layers according to the determined type of the anatomical feature, and detecting structures of the decided layers in the tomogram, and means for modifying the structure of the layer included in a region having the anatomical feature of the structures of the layers detected by the layer structure detection means.

24 Claims, 12 Drawing Sheets

(51) Int. Cl.
*G06T 7/60* (2006.01)
*G01N 21/47* (2006.01)

(56) References Cited

FOREIGN PATENT DOCUMENTS

| JP | 2008-073099 A | 4/2008 |
| JP | 2008-154704 A | 7/2008 |
| JP | 2009-061203 A | 3/2009 |
| JP | 2009-066015 A | 4/2009 |
| JP | 2009-089792 A | 4/2009 |

OTHER PUBLICATIONS

Kavitha et al., "Automatic detection of optic disc and exudates in retinal images", Jan. 7, 2005, Proc. of 2005 Int. Conf. on Intelligent Sensing and Information Processing 2005, p. 501-506.*
Fleckenstein et al., "High-Resolution Spectral DOmain-OCT Imaging in Geographic Atrophy Associated with Age-Related Macular Degeneration", Sep. 2008, Association for Research in Vision and Opthalmology, Investigative Opthamlmology & Visual Science, vol. 49, No. 9, p. 4137-4144.*
Office Action for Counterpart Korean Application No. 10-2011-7030982, dated Dec. 13, 2012.

* cited by examiner

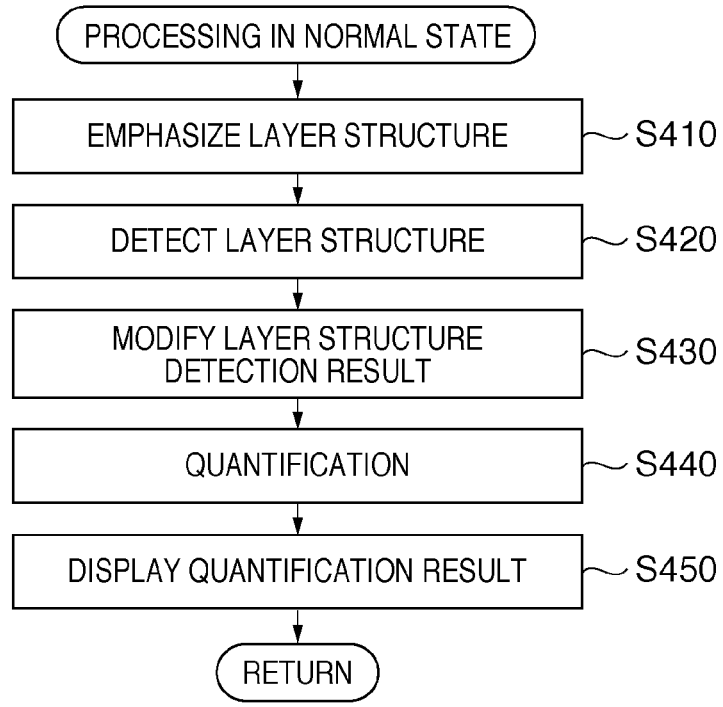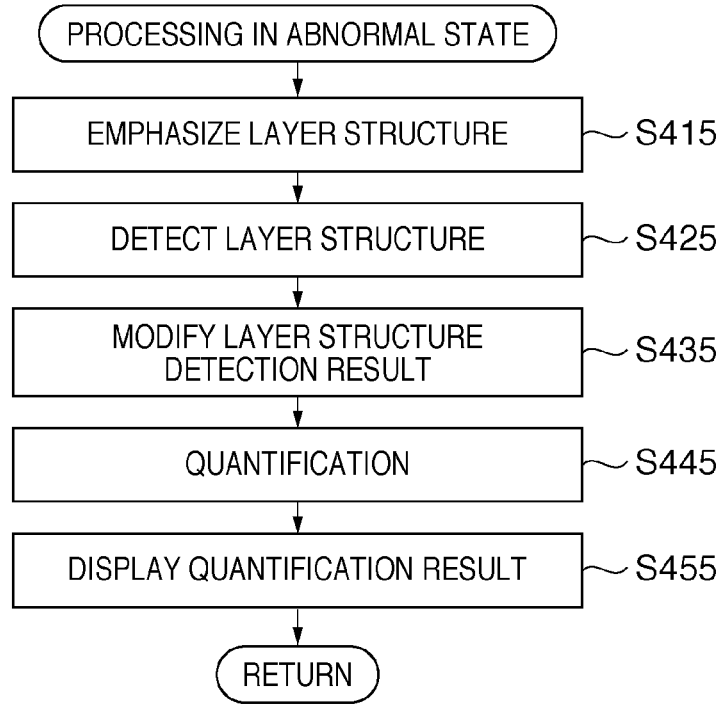

FIG. 6
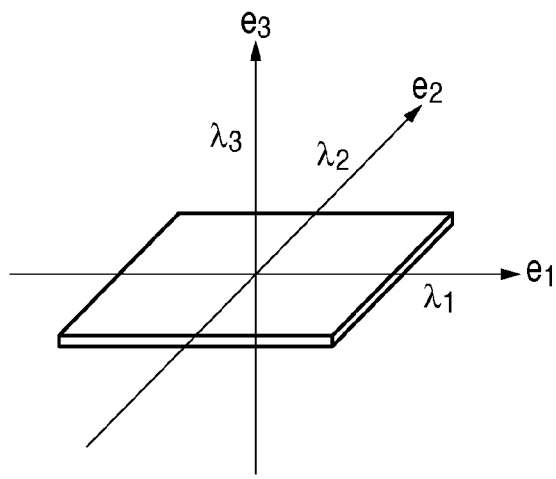
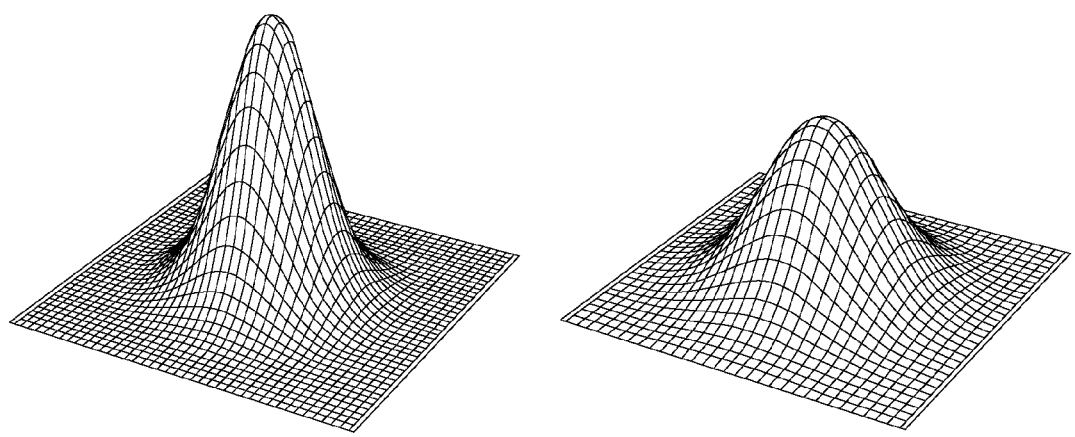
FIG. 7A          FIG. 7B
 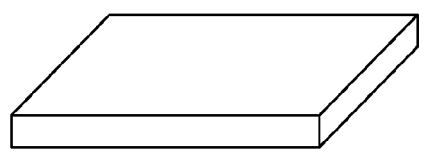
FIG. 7C          FIG. 7D

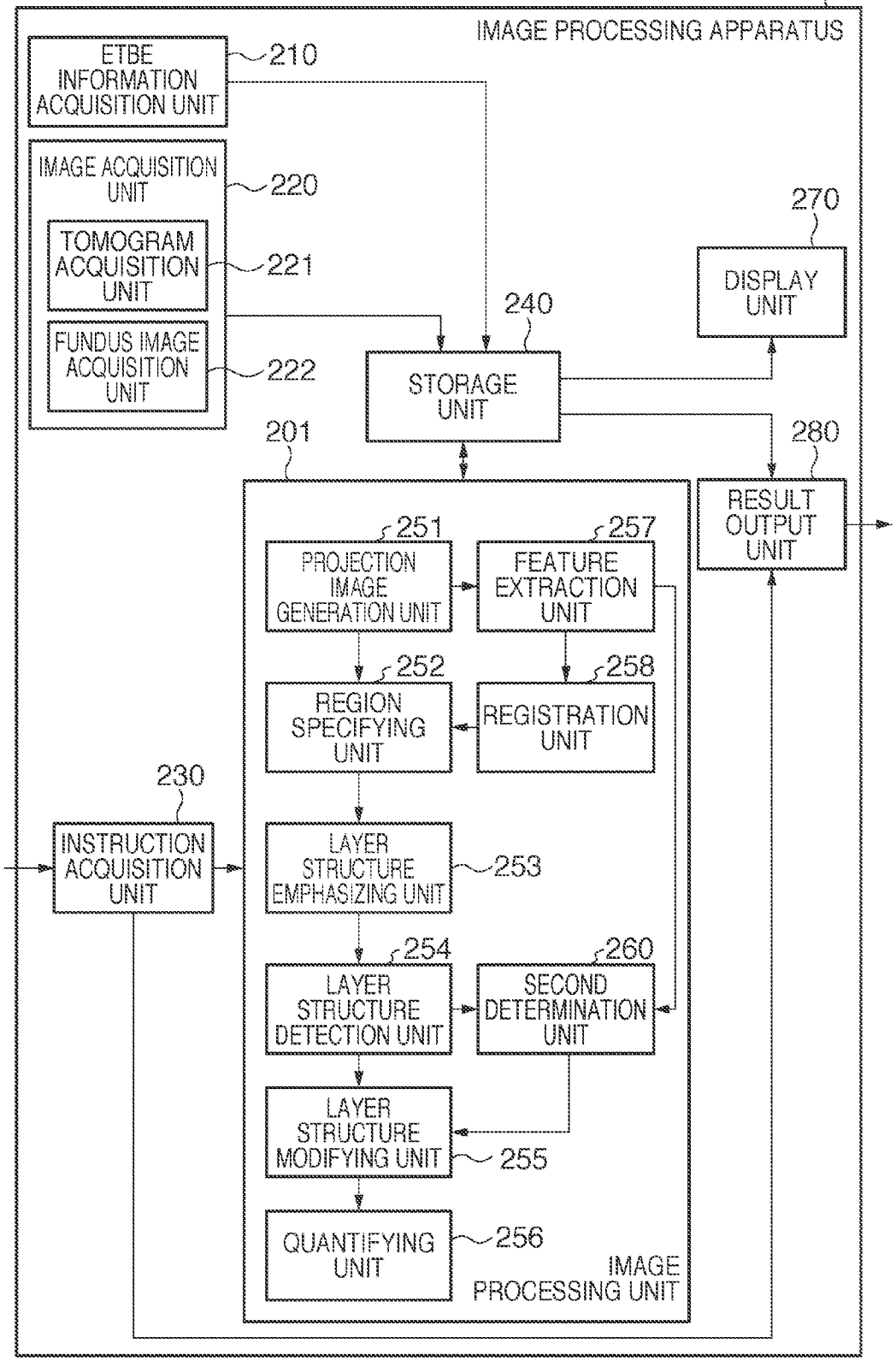

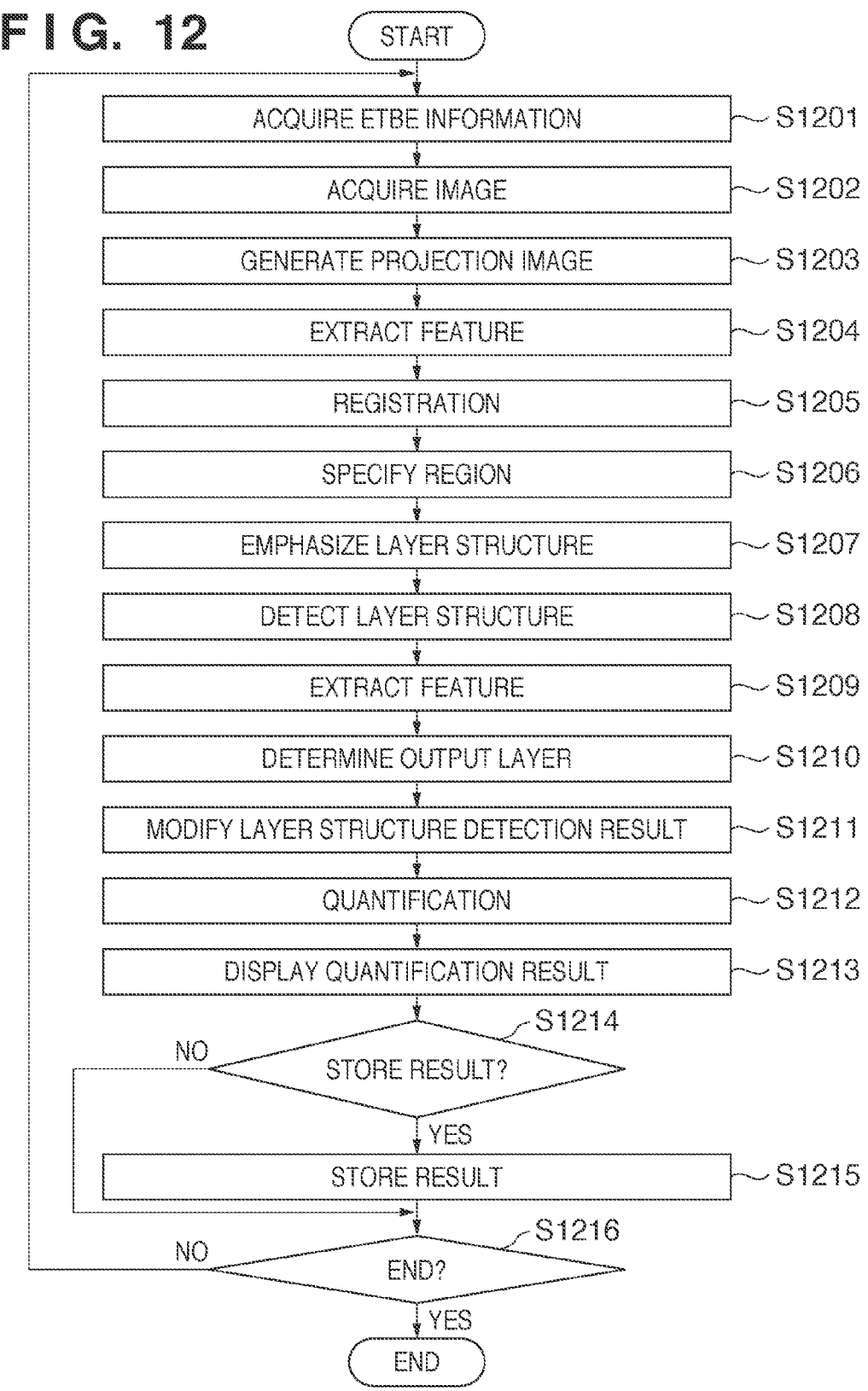

IMAGE PROCESSING APPARATUS, CONTROL METHOD, AND COMPUTER READABLE STORAGE MEDIUM FOR ANALYZING RETINA LAYERS OF AN EYE

TECHNICAL FIELD

The present invention relates to an image processing apparatus, control method thereof, and computer program.

BACKGROUND ART

Ophthalmic examinations are commonly made for the early diagnosis of various diseases that come before lifestyle-related diseases and causes of blindness. Since a medical examination or the like is required to find a disease in a whole eye portion, an examination using an image over a broad range of the eye portion (to be referred to as a fundus image hereinafter) is indispensable. The fundus image is captured using a fundus camera or SLO (Scanning Laser Opthalmoscope). On the other hand, a tomography apparatus for an eye portion such as an OCT (Optical Coherence Tomography) is expected to effectively give more adequate diagnoses of diseases since it allows to three-dimensionally observe the state of the interior of retina layers.

FIG. 5A is a pattern diagram of a macula tomogram of a retina captured by the OCT. A tomogram of an eye portion by the OCT is three-dimensionally obtained. In FIG. 5A, reference symbols $T_1$ to $T_n$ denote two-dimensional (2D) cross-sectional images (B-scan images) of a macula portion. Then, reference numeral 1 denotes an inner limiting membrane; 2, a boundary between a nerve fiber layer and its underlying layer (to be referred to as a nerve fiber layer boundary 2 hereinafter); and 2', a nerve fiber layer. Reference numeral 3 denotes a boundary between an inner plexiform layer and its underlying layer (to be referred to as an inner plexiform layer boundary 3 hereinafter); and 4, a boundary between an outer plexiform layer and its underlying layer (to be referred to as an outer plexiform layer boundary 4 hereinafter). Reference numeral 5 denotes a junction between inner and outer photoreceptor segments; and 6, a retinal pigment epithelium boundary. For example, when such tomogram is input, if the thickness of the nerve fiber layer 2' ($T_1$ in FIG. 5A) can be measured, a degree of progress of a disease such as glaucoma and a recovery level after a medical treatment can be quantitatively diagnosed. In order to quantitatively measure the thicknesses of these layers, a technique for detecting the boundaries of respective layers of a retina from a tomogram using a computer and measuring the thicknesses of the respective layers is disclosed (see Japanese Patent Laid-Open No. 2008-073099).

On the other hand, in an OCT tomogram, when measurement light is strongly reflected or absorbed by an object, an artifact caused by attenuation or omission of signals is often generated behind the object. Note that the object includes a blood vessel (blood) and exudate. By contrast, a technique which extracts a blood vessel region from a surface image of an eye fundus, back-projects the blood vessel region onto the OCT tomogram, and interpolates layer boundaries in the vicinity of the back-projection region, so as to estimate the layer boundaries in an artifact region caused by the blood vessel has been proposed (see Japanese Patent Laid-Open No. 2007-325831).

On the other hand, it is demanded for an examination using the OCT to detect a plurality of types of ophthalmic diseases such as glaucoma and age-related macular degeneration. Then, since layers of interest in the tomogram are different according to the presence/absence of a disease and the types of diseases, it is demanded to detect layers according to the state of a retina.

SUMMARY OF INVENTION

With the methods described in Japanese Patent Laid-Open Nos. 2008-073099 and 2007-325831, in order to cope with detection of a plurality of types of diseases, an operator has to estimate a disease in advance, and has to perform a measurement in an analysis mode suited to that disease. When a proper processing result cannot be obtained, the operator has to perform a re-measurement by changing the analysis mode to that suited to another disease and changing image processing parameters, resulting in troublesome processing. For this reason, large quantities of data are to be analyzed, a tremendous load is imposed on the user. Furthermore, the method described in Japanese Patent Laid-Open No. 2008-073099 above does not disclose any method of calculating a layer boundary of a region where an artifact is generated.

The method described in Japanese Patent Laid-Open No. 2007-325831 above handles all regions which are back-projected onto the OCT tomogram as artifact regions (blood vessel immediately beneath regions), and interpolates layer boundaries to estimate them without detecting any tomogram in those regions. For this reason, when no signal attenuation occurs on each back-projection region on the tomogram, the layer boundary result becomes inaccurate. Also, the above method copes with only signal attenuation due to a blood vessel, but it does not cope with any signal attenuation due to morbid portions such as an exudate and bleeding.

Hence, the present invention selects types of layers to be detected according to the state of a retina of an eye to be examined, and detects layers based on anatomical features of retina layers, thus allowing high-precision detection of layer boundaries as well as an attenuation region.

One aspect of embodiments of the present invention relates to an image processing apparatus, which analyzes retina layers of an eye to be examined, comprising, feature extraction means for extracting a feature amount, which represents an anatomical feature in the eye to be examined, from a projection image obtained from a tomogram of the retina layers and a fundus image of the eye to be examined, determination means for determining a type of the anatomical feature based on the feature amount, layer structure detection means for deciding layers to be detected from the retina layers according to the determined type of the anatomical feature, and detecting structures of the decided layers in the tomogram, and layer structure modifying means for modifying the structure of the layer included in a region having the anatomical feature of the structures of the layers detected by the layer structure detection means.

Another aspect of embodiments of the present invention relates to an image processing apparatus, which analyzes retina layers of an eye to be examined, comprising, feature extraction means for extracting a feature amount, which represents an anatomical feature in the eye to be examined, from a projection image obtained from a tomogram of the retina layers, layer structure detection means for detecting structures of layers in the retina layers from the tomogram, information extraction means for extracting information of intensities and information of a shape of a layer between predetermined layers based on the structures of the layers detected by the layer structure detection means, determination means for determining a presence/absence and a type of a morbid portion in the retina layers based on the feature amount, the information of the intensities, and the information of the shape, and layer structure modifying means for modifying the structures of the layers detected by the layer structure detection means, in accordance with the determination result of the determination means, wherein when the determination means determines that the morbid portion exists, the layer structure modifying means modifies structures of some of the layers detected by the layer structure detection means.

Further features of the present invention will become apparent from the following description of exemplary embodiments (with reference to the attached drawings).

BRIEF DESCRIPTION OF DRAWINGS

FIGS. 4A and 4B are flowcharts showing the processes at the time of normal and abnormal states in the layer structure analysis processing sequence;

FIG. 6 is a view showing the relationship between eigenvalues and eigenvectors required to generate a layer structure-emphasized image according to the embodiment;

FIGS. 7A to 7D are views for explaining generation of a multiresolution layer structure-emphasized image according to the embodiment;

FIG. 11 is a block diagram showing the functional arrangement of an image processing apparatus 11 according to the second embodiment;

FIG. 12 is a flowchart showing the retina layer structure analysis processing sequence according to the second embodiment.

DESCRIPTION OF EMBODIMENTS

The best mode for carrying out the present invention will be described in detail hereinafter with reference to the drawings. However, the scope of the invention is not limited to illustrated examples.

According to one aspect of an embodiment of the invention, an image processing apparatus 10 acquires a tomogram and fundus image of an eye to be examined, and generates a projection image from the tomogram so as to perform registration between the tomogram and fundus image. Then, the apparatus 10 detects anatomical information required to determine the presence/absence and type of a disease from the fundus image and projection image, determines layers to be measured based on the detection result, and executes analysis processing of predetermined layers. Note that this embodiment will explain a tomogram in which a macula portion appears. However, a portion to be captured is not limited to a macula portion, but the same processing may be applied to an optic papilla. Furthermore, processing is applicable to an image in which a macula portion and optic papilla appear at the same time. Also, a case will be described wherein analysis processing is applied to the entire three-dimensional (3D) tomogram to be acquired. However, in another arrangement, a two-dimensional (2D) tomogram of interest (the 2D tomogram will be referred to as a cross-sectional image hereinafter) may be selected from the 3D tomogram, and processing may be applied to the selected cross-sectional image. For example, processing may be applied to a cross-sectional image including a specific portion (for example, a central fovea) of an eye fundus, which is determined in advance. In this case, boundaries and normal structures of layers to be detected, data in a normal state, and the like are 2D data on that cross-section.

Figure 1:
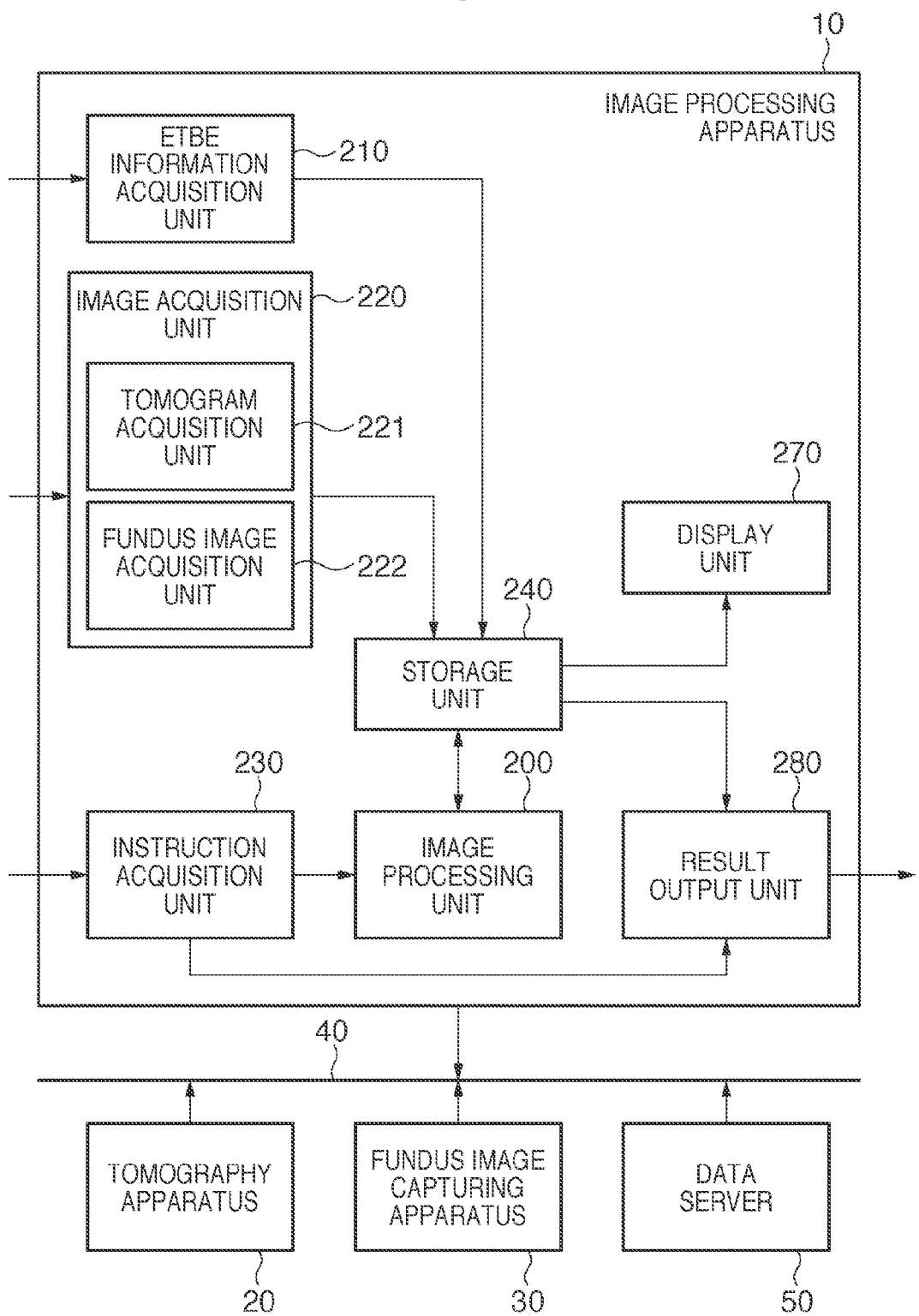
FIG. 1 is a block diagram showing an example of the functional arrangement of an image processing system according to an embodiment.

The image processing apparatus 10 shown in FIG. 1 is connected to a tomography apparatus 20, fundus image capturing apparatus 30, and data server 50 via a local area network (LAN) 40 such as Ethernet® to build up an image processing system. Note that the image processing apparatus 10 may be connected to these apparatuses via an interface such as an optical fiber, USB, or IEEE1394. Also, the image processing apparatus 10 may be connected to these apparatuses via an external network such as the Internet.

The tomography apparatus 20 obtains a tomogram of an eye portion, and includes, for example, a time domain OCT or Fourier domain OCT. The fundus image capturing apparatus 30 captures a fundus image of an eye portion, and includes, for example, a fundus camera or SLO. The data server 50 holds tomograms, image feature amounts, and the like of an eye to be examined. The data server 50 stores tomograms of an eye to be examined output from the tomography apparatus 20, and analysis results output from the image processing apparatus 10. Also, the data server 50 transmits previous data associated with an eye to be examined to the image processing apparatus 10 in response to a request from the image processing apparatus 10.

Respective functional blocks which configure the image processing apparatus 10 will be described below. An image processing unit 200 performs a disease determination of an eye fundus by detecting feature amounts of morbid portions and blood vessels from a fundus image, and executes processing for analyzing predetermined layers for a tomogram according to the determination result. An ETBE (eye to be examined) information acquisition unit 210 externally acquires information used to identify an eye to be examined. An image acquisition unit 220 includes a tomogram acquisition unit 221 and fundus image acquisition unit 222. The image acquisition unit 220 acquires a tomogram transmitted from the tomography apparatus 20 and a fundus image transmitted from the fundus image capturing apparatus 30. An instruction acquisition unit 230 acquires a processing instruction input by an operator. A storage unit 240 temporarily holds the information associated with an eye to be examined acquired by the ETBE information acquisition unit 210 and the tomogram and fundus image of the eye to be examined acquired by the image acquisition unit 220. A display unit 270 displays the tomogram acquired by the image acquisition unit 220 and the processing result of the tomogram by the image processing unit 200 on a monitor. A result output unit 280 associates an examination date and time, information used to identify the eye to be examined, the tomogram of the eye to be examined, and the analysis result obtained by the image processing unit 200 with each other as information to be stored, and transmits that information to the data server 50.

Figure 2:
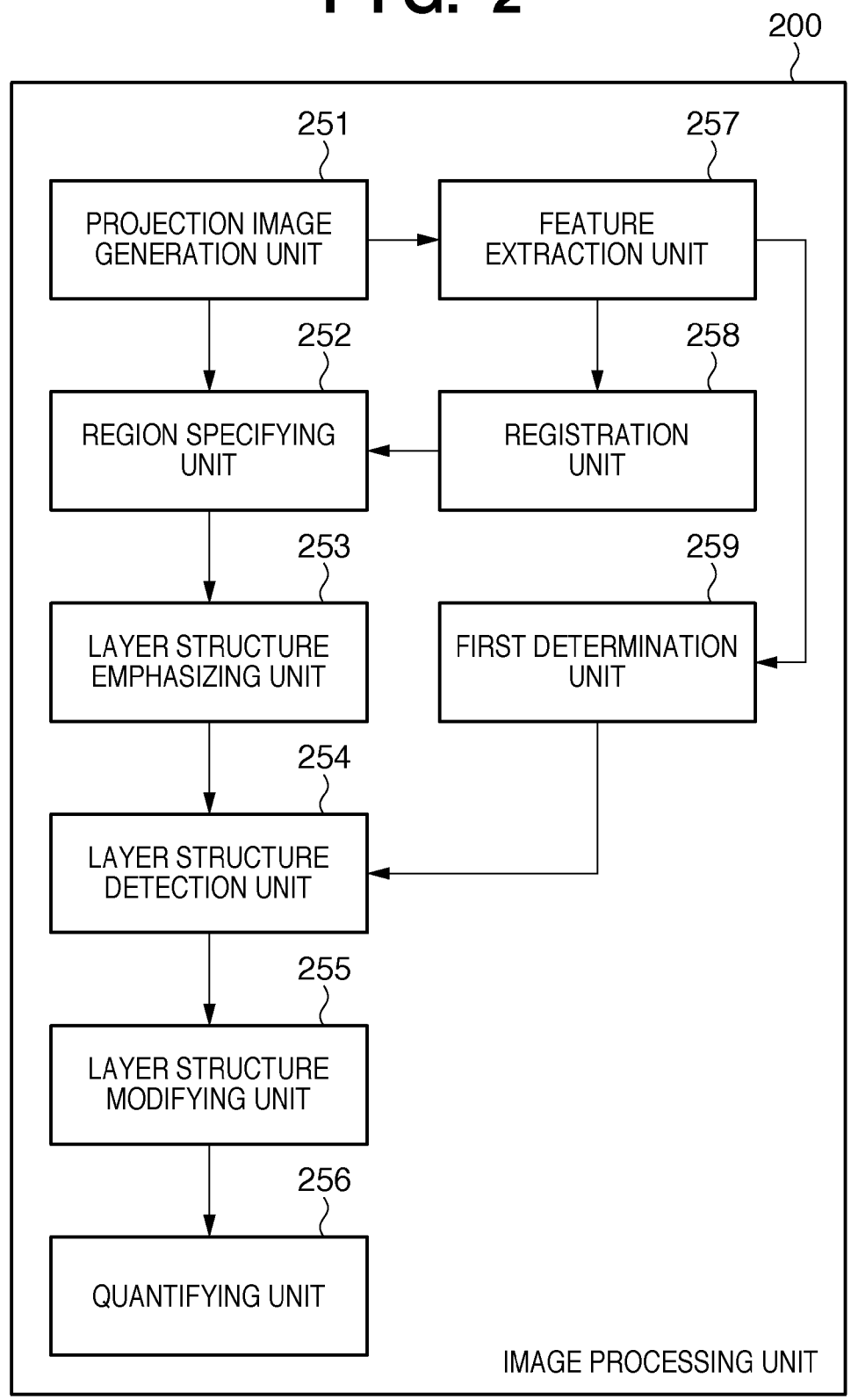
FIG. 2 is a block diagram showing the functional arrangement of an image processing unit 200 according to the embodiment.

Respective functional blocks which configure the image processing unit 200 will be described below with reference to FIG. 2. A projection image generation unit 251 generates a projection image by integrating a tomogram in the depth direction, so as to perform registration between a fundus image and the tomogram. A region specifying unit 252 specifies regions of morbid portions and blood vessels in the tomogram based on an extraction result of a feature extraction unit 257. A layer structure emphasizing unit 253 emphasizes layer structures of a retina from the tomogram based on an anatomical feature indicating that the retina includes the layer structures. A layer structure detection unit 254 detects predetermined layers from the tomogram so as to quantify the thicknesses, volumes, and the like of retina layers. A layer structure modifying unit 255 modifies the detection results of the layers detected by the layer structure detection unit 254 at, for example, a position where a signal intensity attenuation occurs in a region of the tomogram. A quantifying unit 256 calculates layer thicknesses, areas, and volumes based on the results of the layer structure detection unit 254. The feature extraction unit 257 detects blood vessels and morbid portions from the projection image generated by the projection image generation unit 251 and the fundus image captured by the fundus image capturing apparatus 30. The morbid portions include an exudate, druse, and bleeding. A registration unit 258 performs registration between the projection image and fundus image based on blood vessel features and feature portions extracted by the feature extraction unit 257. A first determination unit 259 determines types of layers to be detected by the layer structure detection unit 254 based on the features extracted by the feature extraction unit 257. Note that the contents of the detailed processes to be executed by the respective functional blocks will be described in detail later.

The processing sequence of the image processing apparatus 10 will be described below with reference to the flowchart shown in FIG. 3. The processing sequence acquires a tomogram and fundus image of an eye to be examined, and generates a projection image from the tomogram so as to perform registration between the tomogram and fundus image. Then, the processing sequence detects anatomical information required to determine the presence/absence and type of a disease from the fundus image and projection image, determines layers to be measured based on the determination result, and executes analysis processing of predetermined layers.

In step S301, the ETBE information acquisition unit 210 externally acquires an object identification number as information used to identify an eye to be examined. The unit 210 acquires information associated with the eye to be examined held by the data server 50 based on the object identification number. The information associated with the eye to be examined includes, for example, the name, age, gender, and right or left eye as an examination target of a patient. Furthermore, when measurement data of visual acuities, axial lengths, ocular pressures, and the like are available as another examination information, the unit 210 may acquire these measurement data. Then, the unit 210 transmits the acquired information to the storage unit 240.

In step S302, the tomogram acquisition unit 221 acquires a tomogram transmitted from the tomography apparatus 20, and the fundus image acquisition unit 222 acquires a fundus image transmitted from the fundus image capturing apparatus 30. These units 221 and 222 transmit the acquired information to the storage unit 240. The following description will be given under the assumption that the tomogram and fundus image acquired by the image acquisition unit 220 are those of the eye to be examined identified by the ETBE information acquisition unit 210. Also, assume that the tomogram includes various parameters associated with tomography as information, and the fundus image includes various parameters associated with its capturing as information.

Figure 5A:
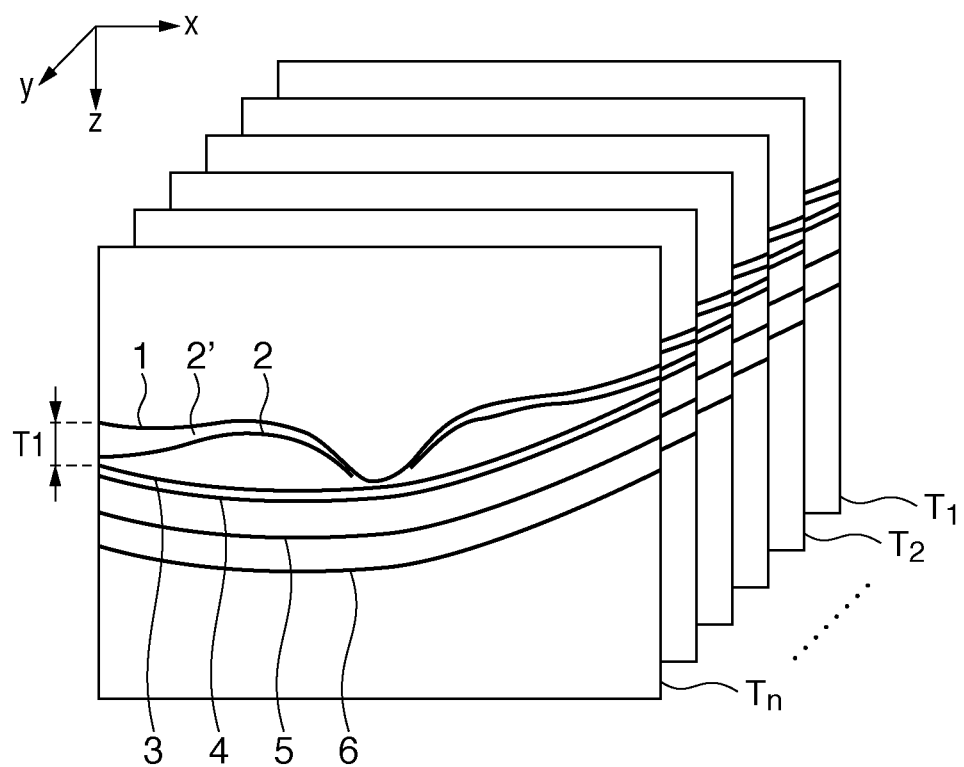
FIGS. 5A and 5B are schematic views showing examples of a tomogram and projection image according to the embodiment.
Figure 5B:
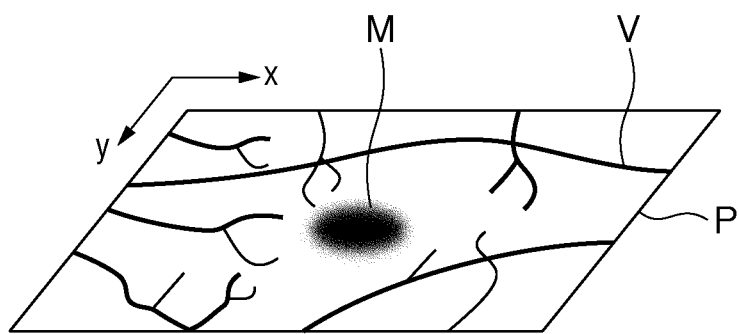

In step S303, the projection image generation unit 251 generates a projection image by integrating respective cross-sectional images (for example, B-scan images) in the depth direction, so as to perform registration between the fundus image and tomogram. The processing of the projection image generation unit 251 will be described below with reference to FIGS. 5A and 5B. FIGS. 5A and 5B show examples of a tomogram and projection image. FIG. 5A shows cross-sectional images $T_1$ to $T_n$, and FIG. 5B shows a projection image P generated based on the cross-sectional images $T_1$ to $T_n$. The depth direction agrees with a z-direction in FIG. 5A, and integrating images in the depth direction is processing for summing up light intensities (luminance values) at respective depth positions in the z-direction of FIG. 5A. The projection image P may be defined by values obtained by simply adding intensities at respective depth positions or average values obtained by dividing the sums by the number of additions. To obtain the projection image P, intensities of not all pixels need be added in the depth direction, but intensities of pixels within only an arbitrary range may be added. For example, the entire retina layers may be detected in advance, and intensities in only the retina layers may be added. Furthermore, intensities in only arbitrary layers in the retina layers may be added. The projection image generation unit 251 generates the projection image P by executing the processing for integrating the n cross-sectional images $T_1$ to $T_n$ captured by the tomography apparatus 20 in the depth direction. The projection image P in FIG. 5B expresses that a larger integrated value represents a higher intensity and a smaller integrated value represents a lower intensity. A curve V in the projection image P in FIG. 5B represents a blood vessel, and a circle M at the center of the image represents a macula portion. The tomography apparatus 20 captures the cross-sectional images $T_1$ to $T_n$ of the eye portion by receiving reflected light of light emitted by a low-coherence light source using a light-receiving element. At a location where the blood vessel exists, reflected light intensities of light at positions deeper than the blood vessel tend to become weak, and a value obtained by integrating them in the z-direction is smaller than that at a location where no blood vessel exists. For this reason, by generating the projection image P, an image having a contrast between the blood vessel and other portions can be obtained.

In step S304, the feature extraction unit 257 extracts feature amounts which represent blood vessels and morbid portions from the projection image generated by the projection image generation unit 251 and the fundus image captured by the fundus image capturing apparatus 30. The morbid portions include an exudate, druse, and bleeding. In an OCT tomogram, artifacts caused by attenuation or omissions of signals are often generated behind absorbing substances such as these blood vessels and morbid portions. For this reason, the feature amounts which well express them are extracted from the fundus image and projection image, and these regions are used as mask regions upon deciding layer structures. Furthermore, these feature amounts can also be used as features upon registration between the fundus image and projection image in next step S305. Since a blood vessel has a thin linear structure, it is extracted using a filter that emphasizes the linear structure. As the filter that emphasizes the linear structure, a filter, which calculates a difference between an average value of image density values in a line segment assumed as a structural element, and an average value in a local region that surrounds the structural element, is used. However, the present invention is not limited to this, and a differential filter such as a Sobel filter may be used. Alternatively, eigenvalues of a Hessian matrix may be calculated for respective pixels of a density value image, and a linear region may be extracted based on combinations of two eigenvalues obtained as results. Furthermore, tophat operations which simply have a line segment as a structural element may be performed.

As image features, an exudate region as a morbid portion locally exists in the fundus image, and has higher intensities than a surrounding region. Hence, exudate extraction can be attained by focusing attention on such image features. Various extraction methods are available. For example, a method of applying tophat operations to one of R, G, and B components of the fundus image is available. The tophat operations calculate density value differences for respective pixels between an original image and output image obtained by applying morphological operations to a density image. In the image after application of the tophat operations, since pixels included in an exudate have signals higher than other pixels, an exudate region can be extracted by applying threshold processing to this image.

With the above processing, feature amounts which well express the exudate region can be extracted. A druse, bleeding, and the like can be similarly extracted as anatomical feature amounts. As the anatomical features obtained from the fundus image, the druse has a white massive image feature. As image features of a bleeding region, the bleeding region has lower density values in respective R, G, and B components than a non-bleeding region, and a heavy bleeding region has considerably lower density values than those of a blood vessel portion. In this way, the morbid portions such as an exudate, druse, and bleeding can be extracted while focusing on pixel values of the projection image.

The extraction method of the feature amounts which express these blood vessels and morbid portions is not limited to the aforementioned method. Also, the method need not be limited to only one method, and a plurality of methods may be combined. As for the morbid portions, they need only be extracted from either the projection image or fundus image, and morbid positions in the tomogram can be specified by combining both the extraction results.

Note that the feature extraction unit 257 may extract a macula portion, optic papilla, and the like in addition to the blood vessels and morbid portions. The registration unit 258 may use these macula portion and optic papilla position as feature amounts upon registration between the projection image and fundus image, or they may be used as feature amounts so as to reduce detection errors of morbid portions. When effective feature amounts (blood vessels and morbid portions) used in layer structure detection cannot be extracted from the fundus image, the process in step S306 is executed while skipping that in next step S305.

In step S305, the registration unit 258 performs registration between the projection image and fundus image. When the fundus image is defined as a reference image, the registration between the projection image and fundus image can be attained by calculating a scale $(S_x, S_y)$, position coordinates (x, y), and rotation (rot) parameters of the projection image. In order to register the positions of the images, regions having anatomical features are extracted. As one of representative anatomical features, the present invention focuses attention on blood vessels. Using the blood vessels respectively extracted from the projection image and fundus image, the images are registered. Upon performing the registration, an evaluation value which represents a similarity between two images is defined in advance, and images are deformed to obtain the best evaluation value. As the evaluation value, a value which represents a degree of overlapping between the projection image blood vessel regions and fundus image blood vessel regions obtained by the above processing, a distance between corresponding landmarks upon focusing attention on regions having characteristic geometric shapes such as branch portions of blood vessels, and the like can be used. In this embodiment, a blood vessel is used as a region having an anatomical feature. Alternatively, another anatomical feature such as an optic papilla region, or an exudate or bleeding region caused by a disease may be used. Furthermore, in place of focusing attention on only anatomical features such as blood vessels, an evaluation value calculated from the entire images, for example, a mean square error, correlation coefficient, or mutual information content of intensities can be used.

In step S306, the region specifying unit 252 back-projects the blood vessels and morbid portions extracted by the feature extraction unit 257 onto the OCT tomogram. As a result, the blood vessels and morbid portions obtained from the fundus image and projection image can be set on the tomogram as mask regions. The first determination unit 259 determines in step S307 using the feature amounts extracted by the feature extraction unit 257 whether or not a morbid portion is detected and a type of the detected morbid portion, and selects types of layers to be detected by the layer structure detection unit 254. In order to determine the presence/absence and type of a morbid portion, an identifier such as a Support Vector Machine or an identifier ensemble built based on, for example, AdaBoost is used. For example, when an exudate region is to be extracted, output results of various image filters, which can emphasize a region in which density values of R, G, and B components of the fundus image or intensity contrasts in R, G, and B components are high, are used as feature amounts. Then, whether or not each pixel belongs to an exudate is determined using the identifier or its ensemble. Furthermore, all pixels, which are determined to belong to an exudate, undergo clustering to identify again whether or not each cluster belongs to an exudate region. At this time, an average or variance of intensities in each cluster or an intensity contrast between regions inside and outside each cluster is used as a feature amount.

When no morbid portion is detected as the determination result of the first determination unit 259, the layer structure detection unit 254 detects the inner limiting membrane 1, nerve fiber layer boundary 2, inner plexiform layer boundary 3, outer plexiform layer boundary 4, junction 5 between inner and outer photoreceptor segments, and retinal pigment epithelium boundary 6. When a morbid portion is detected, the unit 254 detects the inner limiting membrane 1 and retinal pigment epithelium boundary 6. Furthermore, when a druse is detected as a morbid portion, since the retina suffers age-related macular degeneration, the retinal pigment epithelium boundary 6 has a concave-convex shape. For this reason, a normal structure of the retinal pigment epithelium boundary 6 is estimated simultaneously with detection of the retinal pigment epithelium boundary 6. If the first determination unit 259 determines that the state of an eye fundus is normal, the process advances to step S308; if it determines that the state of the eye fundus is abnormal, the process advances to step S309.

In step S308, analysis processing when the state of the retina is normal is executed. The processing in this step will be described later with reference to the flowchart shown in FIG. 4A. In step S309, analysis processing when the state of the retina is abnormal is executed. The processing in this step will be described later with reference to the flowchart shown in FIG. 4B. In step S310, the instruction acquisition unit 230 externally acquires an instruction as to whether or not the result of the current processing associated with the eye to be examined is stored in the data server 50. This instruction is input by an operator using a user interface (not shown). If the operator instructs to store the result, the process advances to step S311; otherwise, the process jumps to step S312.

In step S311, the result output unit 280 associates a date and time of examination, the information used to identify the eye to be examined, the tomogram and fundus image of the eye to be examined, and the analysis result obtained by the image processing unit 200 with each other as information to be stored, and transmits that information to the data server 50. In step S312, the instruction acquisition unit 230 externally acquires an instruction as to whether or not the tomogram analysis processing by the image processing apparatus 10 is to end. This instruction is input by an operator using a user interface (not shown). If the unit 230 acquires an instruction to end the processing, the image processing apparatus 10 ends its processing. On the other hand, if the unit 230 acquires an instruction to continue the processing, the process returns to step S301 to execute processing for the next eye to be examined (or re-processing for the current eye to be examined). As described above, the processing of the image processing apparatus 10 is executed.

Details of the processing contents in step S308 will be described below with reference to FIG. 4A. In step S410, the layer structure emphasizing unit 253 emphasizes the layer structures of the retina from the tomogram. In order to emphasize the layer structures of the retina, a layer structure emphasizing filter based on eigenvalues of a Hessian matrix is used. This filter can emphasize a secondary local structure of a 3D density distribution based on the relationship among three eigenvalues ($\lambda_1$, $\lambda_2$, $\lambda_3$) of the Hessian matrix. The Hessian matrix is given by:

$$H = \begin{pmatrix} I_{xx} & I_{xy} & I_{xz} \\ I_{yx} & I_{yy} & I_{yz} \\ I_{zx} & I_{zy} & I_{zz} \end{pmatrix} \quad (1)$$

The Hessian matrix is a square matrix made by the entire second partial derivatives of a multi-variable function. I is a density value of an image. FIG. 6 shows the relationship between the eigenvalues of the Hessian matrix and eigenvectors ($e_1$, $e_2$, $e_3$). The relationship among the eigenvalues of the Hessian matrix is described by:

$$\lambda_3 \leq \lambda_2 \leq \lambda_1 \quad (2)$$

A conditional formula for the eigenvalues required to emphasize the layer structure is described by:

$$\lambda_3 \ll \lambda_2 \doteq \lambda_1 \doteq 0 \quad (3)$$

The layer structure of the retina can be emphasized by calculating, from the three eigenvalues calculated by these equations:

$$S_{sheet}\{f\} = \begin{cases} |\lambda_3| \cdot \omega(\lambda_2; \lambda_3) \cdot \omega(\lambda_1; \lambda_3) & \lambda_3 < 0 \\ 0 & \text{otherwise} \end{cases} \quad (4)$$

where $\omega(\lambda_s; \lambda_t)$ is a weighting function, which is given by:

$$\omega(\lambda_s; \lambda_t) = \begin{cases} \left(1 + \frac{\lambda_s}{|\lambda_t|}\right)^\gamma & \lambda_t \leq \lambda_2 \leq 0 \\ \left(1 - \alpha \frac{\lambda_s}{\lambda_t}\right)^\gamma & \frac{|\lambda_t|}{\alpha} > \lambda_s > 0 \\ 0 & \text{otherwise} \end{cases} \quad (5)$$

where $\gamma$ and $\alpha$ are weights.

Furthermore, in order to cope with retina layers with various thicknesses, a multiresolution layer structure emphasizing filter can be used. For this purpose, the eigenvalues of the Hessian matrix for smoothed images by Gaussian functions $G(x; \sigma_f)$ of a plurality of resolutions $\sigma_f$ need only be analyzed. Note that x is (x, y, z). FIGS. 7A and 7B show Gaussian functions having different resolutions $\sigma_f$, and FIGS. 7C and 7D show images of thicknesses of layers emphasized by these functions. FIG. 7C shows the thickness of the layer emphasized by the Gaussian function shown in FIG. 7A, and FIG. 7D shows the thickness of the layer emphasized by the Gaussian function shown in FIG. 7B. The resolution in FIG. 7A is $\sigma_a$, that in FIG. 7B is $\sigma_b$, and the relation between the two resolutions is as described by:

$$\sigma_a < \sigma_b \quad (6)$$

An equation of a smoothed image by the Gaussian function is described by:

$$I_{xx} = \frac{\partial^2}{\partial x^2} G(x; \sigma_f) * I(x) \quad (7)$$

Equation (7) describes one component in the Hessian matrix, and other components can be calculated in the same manner as in equation (7). A plurality of resolutions $\sigma_f$ are set in equation (7), and equations (1) and (4) are solved at the respective resolutions, thus emphasizing retina layers having thicknesses corresponding to the respective resolutions. The results of the plurality of resolutions $\sigma_f$ are combined by:

$$S_{sheet}(x) = \max_i \{\sigma_i^2 S_{sheet}(x; \sigma_i)\} \quad (8)$$

Then, one output can cope with retina layers having various thicknesses. In equation (8), the reason why $\sigma_i^2$ is multiplied is to attain normalization processing. i ranges from 1 to n, and corresponds to the number n of set resolutions.

This embodiment has explained the processing for combining the plurality of resolutions $\sigma_f$ using equation (8). However, the resolutions need not always be combined. For example, the results processed at resolutions suited to the thicknesses of respective layers may be respectively held, and may be selectively used for respective layers. For example, when the tomogram has an image size of 256*240*256, a resolution required to calculate, for example, the inner limiting membrane 1 is 3 or more, and a resolution required to calculate, for example, the inner plexiform layer 3 is 1 to 2. As for the inner limiting membrane 1, an image emphasized using a low resolution may be used. However, using an image obtained by emphasizing the entire retina layers using a high resolution, a probability of a detection error of a cortex of a vitreum peeled from the retina can be reduced.

Figure 8A:
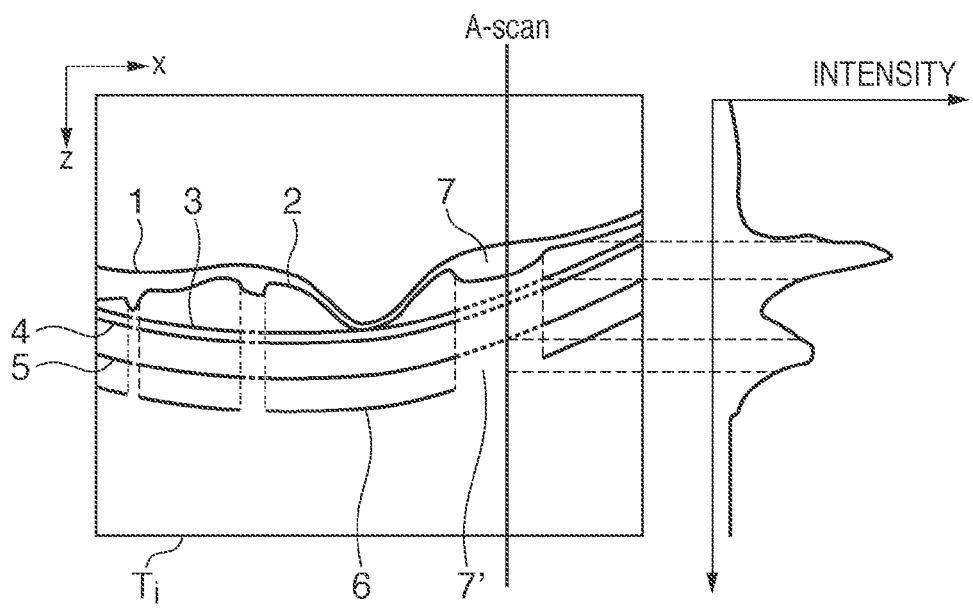
FIGS. 8A and 8B are views for explaining features of a tomogram and those of the layer structure-emphasized image according to the embodiment.
Figure 8B:
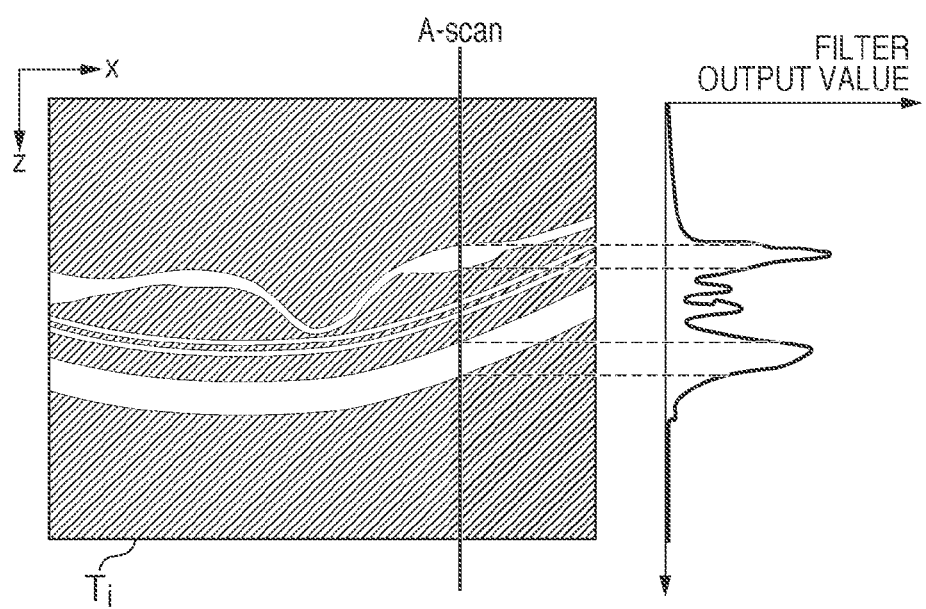

In the above description, the layer structures of the retina are emphasized based on the eigenvalues of the Hessian matrix using equations (4) and (5). However, the present invention is not limited to equations (4) and (5) as long as the layer structures are emphasized using the relationship among the eigenvalues. FIG. 8A is a view for explaining features of a tomogram. In FIG. 8A, reference numeral 1 denotes an inner limiting membrane; 2, a nerve fiber layer boundary; 3, an inner plexiform layer boundary; 4, an outer plexiform layer boundary; 5, a junction between inner and outer photoreceptor segments; 6, a retinal pigment epithelium boundary; 7, a blood vessel region; and 7', a region below a blood vessel. The left view of FIG. 8A shows a cross-sectional image $T_i$, and the right view shows a profile of an image along an A-scan at the blood vessel existence position in the left view. That is, the right view shows the relationship between coordinates and intensities on a line indicated by "A-scan". FIG. 8B shows an example obtained by applying the layer structure emphasizing filter to the tomogram shown in FIG. 8A. The left view of FIG. 8B shows a layer structure-emphasized image of the cross-sectional image $T_i$, and the right view shows a profile of filter outputs along an A-scan at the blood vessel existence position in the left view. Using the layer structure emphasizing filter, even when signals are attenuated by the blood vessel, the layer structure can be emphasized unless signal components are lost. Furthermore, noise components other than the layer structure can be reduced.

In step S420, the layer structure detection unit 254 detects the inner limiting membrane 1, nerve fiber layer boundary 2, junction 5 between inner and outer photoreceptor segments, and retinal pigment epithelium boundary 6. The layer structure detection unit 254 detects the respective layers using feature of the layer structure-emphasized image generated by the layer structure emphasizing unit 253 and gradient features of an image obtained by applying smoothing processing and gradient detection processing to the tomogram. As for the inner limiting membrane 1, a peak of the layer structure emphasizing filter is searched for in the depth direction of an eye fundus from the vitreum side, and a first peak position equal to or larger than a threshold is detected as an initial value of the inner limiting membrane 1 and nerve fiber layer boundary 2. From that initial value, a gradient feature is searched for toward the vitreum side, and a gradient peak position is detected as the inner limiting membrane 1. Likewise, as for the nerve fiber layer boundary 2, a gradient feature is searched for from that initial value in the depth direction of the eye fundus, and a gradient peak position is detected as the nerve fiber layer boundary 2. As for the retinal pigment epithelium boundary 6, a peak of the layer structure emphasizing filter is searched for further in the depth direction of the eye fundus, and the last peak position equal to or larger than the threshold is detected as an initial value of the retinal pigment epithelium boundary 6. A gradient feature is searched for from that initial value in the depth direction of the eye fundus, and a gradient peak position is detected as the retinal pigment epithelium boundary 6. Likewise, as for the junction 5 between inner and outer photoreceptor segments, a gradient feature is searched for from that initial value toward the vitreum side, and a gradient peak position is detected as the junction 5 between inner and outer photoreceptor segments.

Next, the outer plexiform layer boundary 4 is detected. As for the outer plexiform layer boundary 4, between the nerve fiber layer boundary 2 and junction 5 between inner and outer photoreceptor segments, the output values of the layer structure emphasizing filter, which meet:

$$\frac{S_{sheet}(x)}{\max S_{sheet\_NFL\_ISOS\_A}} \geq Th \quad (9)$$

are detected as candidate points. Of these candidate points, a point nearest to the position of the eye fundus in the depth direction is detected as the outer plexiform layer boundary 4. In equation (9), Th is a threshold, which ranges from 0 to 1. In this embodiment, Th=0.7. $S_{sheet}(x)$ is an output value of the layer structure emphasizing filter at a pixel (x, y, z). $\max S_{sheet\_NFL\_ISOS\_A}$ is a maximum output value of the layer structure emphasizing filter between the nerve fiber layer boundary 2 and junction 5 between inner and outer photoreceptor segments at each A-scan. The output value of the layer structure emphasizing filter of the outer plexiform layer boundary 4 tends to be larger than that of the inner plexiform layer boundary 3, but these output values have a very small difference. Hence, using an anatomical feature indicating that the outer plexiform layer boundary 4 is located in the depth direction side of the inner plexiform layer boundary 3 as spatial position information, detection errors can be reduced. As for the inner plexiform layer boundary 3, a peak of the layer structure emphasizing filter located between the nerve fiber layer boundary 2 and outer plexiform layer boundary 4 is searched for, and that position is detected as an initial value. Then, a gradient feature is searched for from that initial value in the depth direction of the eye fundus, and a gradient peak position is detected as the inner plexiform layer boundary 3.

Point groups detected in the respective layers undergo outlier removal processing by, for example, a polynomial function and M-estimation. Alternatively, outlier removal processing for calculating an angle between neighboring detected points, and removing points having an angle equal to or larger than a threshold is executed. Since interpolation processing is executed for removed points, a smooth layer is detected. The example using the output results of the layer structure emphasizing filter has been described. However, the results of the layer structure emphasizing filter need not always be used, and the inner limiting membrane 1, nerve fiber layer boundary 2, and the like may be detected by, for example, threshold processing, gradient detection, or a region expansion method. The processing for detecting the inner limiting membrane 1, nerve fiber layer boundary 2, inner plexiform layer boundary 3, outer plexiform layer boundary 4, junction 5 between inner and outer photoreceptor segments, and retinal pigment epithelium boundary 6 in case of a normal eye has been described. However, a boundary between a ganglion cell layer and the inner plexiform layer, an outer limiting membrane, and the like may be detected in addition to the aforementioned layers. Alternatively, only the layers required to analyze the layer thicknesses and areas, such as the inner limiting membrane 1, nerve fiber layer boundary 2, and retinal pigment epithelium boundary 6, may be detected.

Figure 9:
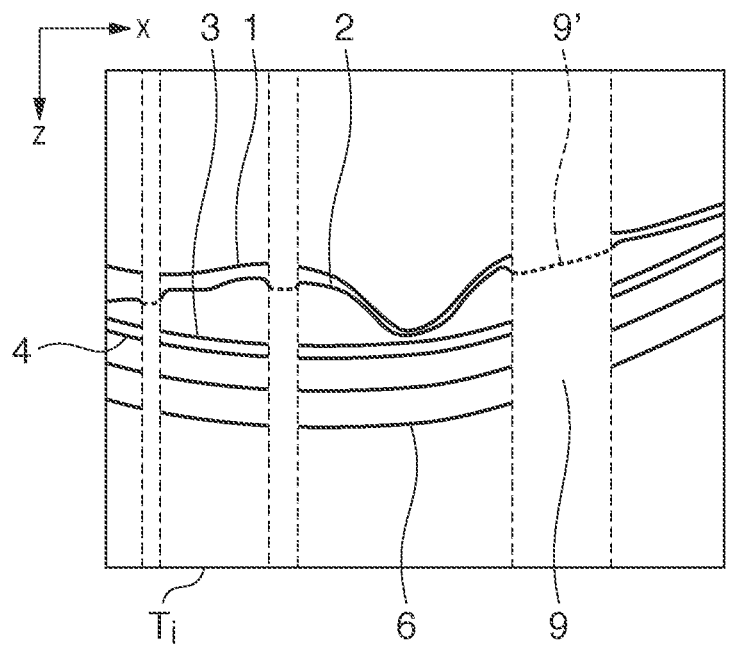
FIG. 9 is a view for explaining a mask region in a tomogram according to the embodiment.

In step S430, the layer structure modifying unit 255 modifies the layer detection results by the layer structure detection unit 254 using the blood vessel detection result by the feature extraction unit 257. FIG. 9 shows an image in which the blood vessel position in FIG. 8A is masked. Referring to FIG. 9, reference numeral 9 denotes a mask region; and 9', a search range in the mask region indicated by a broken line. This mask region 9 is obtained by back-projecting, onto the tomogram, the blood vessel position or positions detected from either or both of the projection image and fundus image by the feature extraction unit 257.

The layer structure modifying unit 255 modifies the detection result of the nerve fiber layer boundary 2 in this mask region 9. The nerve fiber layer boundary 2 is detected while the nerve fiber layer and blood vessel overlap each other, if the blood vessel exists. For this reason, in this region, when the nerve fiber layer boundary 2 is re-detected by searching for a gradient feature in the depth direction of the eye fundus to have a peak of the layer structure emphasizing filter as an initial value, a search range is limited so as not to erroneously detect the blood vessel. The search range is limited by executing interpolation processing from the position of the nerve fiber layer boundary 2 that neighbors the mask region 9. The interpolation processing may use, for example, linear interpolation, spline interpolation, or nonlinear interpolation using a curve of degree n. In this case, it is desirable to limit the search range by a region having a margin in the depth direction by about several pixels from the position calculated by interpolation. By performing boundary detection within the search range, the nerve fiber layer boundary 2 can be detected without erroneously detecting the blood vessel. In this region, not only the search range is limited, but also a threshold of the gradient detection and an algorithm itself of the gradient detection may be changed. Alternatively, the layer structure modifying unit 255 may modify the detection results other than the inner limiting membrane 1 in this mask region. For example, processing for removing points in the mask region, and interpolating each layer by linear or nonlinear interpolation may be executed.

In step S440, the quantifying unit 256 calculates the thicknesses, areas, and volumes of the layers based on the layer boundaries detected by the layer structure detection unit 254. Note that a thickness T1 of the layer (nerve fiber layer 2') can be computed by calculating differences between z-coordinates of the inner limiting membrane 1 and nerve fiber layer boundary 2 at respective coordinate points on an x-z plane. Also, the area of the nerve fiber layer 2' in each cross-sectional image can be computed by adding the layer thicknesses at respective coordinate points in the x-axis direction for respective y-coordinates. Furthermore, the volume of the nerve fiber layer 2' can be computed by adding the calculated areas in the y-axis direction. In this case, the nerve fiber layer 2' has been exemplified, and the thicknesses, areas, and volumes of other layers and the entire retina layers can be similarly calculated.

Furthermore, when previously quantified layer thicknesses, areas, and volumes are available, comparison with the previously quantified data can be made. A comparison method with the previously quantified data in this case will be exemplified below. Initially, previous and current tomograms are registered. The registration of the tomograms can use a known method such as rigid affine deformation or FFD (Free form deformation) as nonlinear deformation. If a positional correspondence with the previously captured tomogram is already determined, the layer thicknesses, areas, and the like of arbitrary sections, and the volumes and the like of arbitrary regions can be compared. In the above description, data are compared after registration with a previous image. However, when the tomography apparatus 20 includes a tracing function, and can capture an image at the same position as the previous position at the time of tomography, no registration is required. Furthermore, comparison between slice numbers of B-scan images or 3D images may be simply made. Assume that the quantifying unit 256 need only calculate at least one of the aforementioned numerical value data, and can arbitrarily set data to be quantified. If no data can be calculated, a quantification failure message may be displayed by the display unit 270 in next step S450.

Figure 10A:
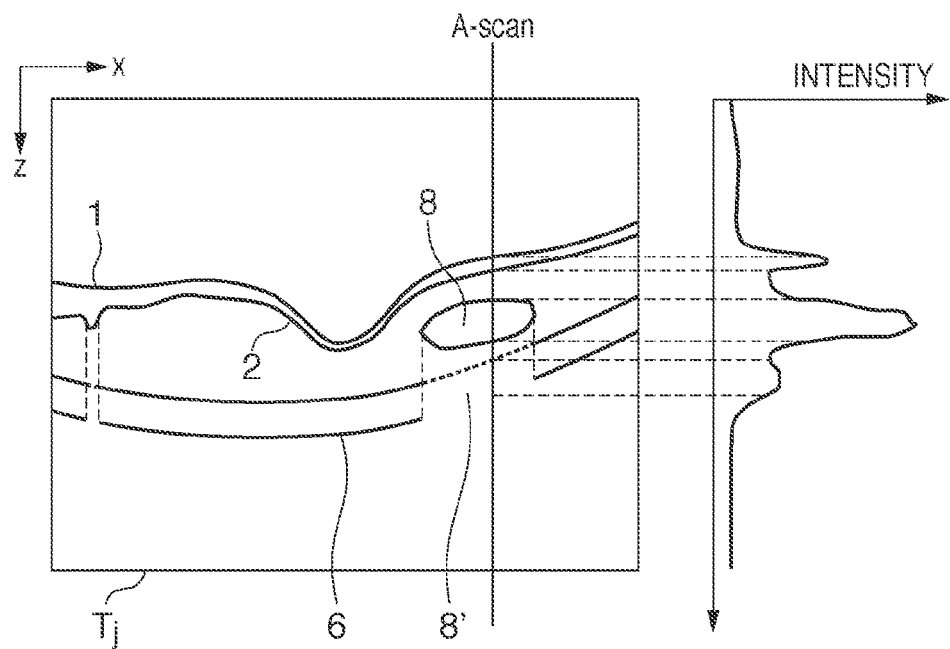
FIGS. 10A and 10B are views for explaining features of the tomogram and the mask region according to the embodiment.

In step S450, the display unit 270 displays the tomogram and fundus image, the detection results of the layers and layer boundaries of the tomogram, and the quantification results in association with the layers of the tomogram. If previous data are available, the display unit 270 may display the current data in comparison with the previous data. Not all the layers and quantification results calculated in steps S420 to S440 need be displayed, and the results may be internally held. The processing sequence executed in the processing in step S309 when the state of the retina is abnormal will be described below with reference to FIG. 4B. Since step S415 is the same as step S410, a description thereof will not be repeated. FIG. 10A shows a case when an exudate is detected as a morbid portion. FIG. 10A is a view for explaining features of a tomogram when an exudate exists. In FIG. 10A, reference numeral 1 denotes an inner limiting membrane; 2, a nerve fiber layer boundary; 6, a retinal pigment epithelium boundary; 8, an exudate region; and 8' a region below the exudate. The left view of FIG. 10A shows a cross-sectional image $T_j$, and the right view shows a profile of an image along an A-scan at the position where the exudate is located in the left view. That is, the right view shows the relationship between the coordinates and intensities on a line indicated by "A-scan".

In step S425, the layer structure detection unit 254 calculates the inner limiting membrane 1 and retinal pigment epithelium boundary 6. Since the layer detection method is the same as that in step S420, a description thereof will not be repeated. Note that layers to be detected when a fundus disease exists are not limited to the inner limiting membrane 1 and retinal pigment epithelium boundary 6, and arbitrary layers may be detected in accordance with a user's instruction.

Figure 10B:
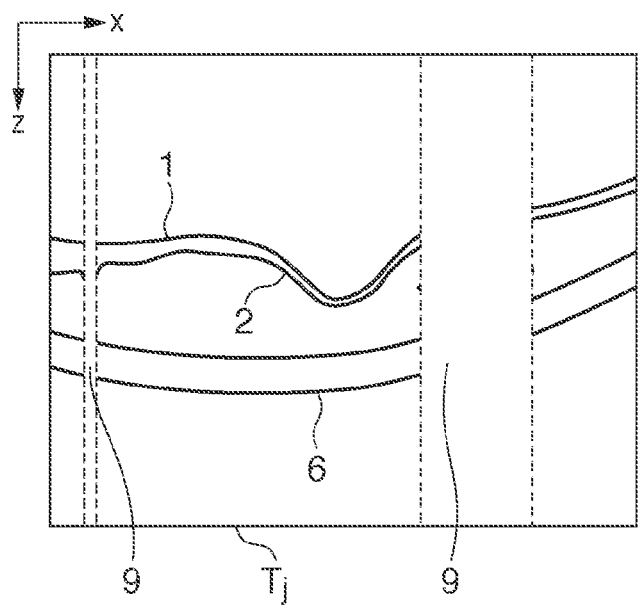

In step S435, the layer structure modifying unit 255 modifies the layer detection results of the layer structure detection unit 254 using the detection results of the blood vessel and exudate (morbid portion) by the feature extraction unit 257. FIG. 10B shows an image obtained masking the exudate and blood vessel positions in FIG. 10A. In FIG. 10B, reference numeral 9 denotes a mask region. This mask is obtained by back-projecting, onto the tomogram, the exudate and blood vessel positions detected from either or both of the tomogram and fundus image by the feature extraction unit 257. The layer structure modifying unit 255 modifies the detection result of the retinal pigment epithelium boundary 6 in this mask region. For example, the unit 255 removes points in the mask region in the morbid region, and then interpolates the retinal pigment epithelium boundary 6 using a remaining point group or curve. Thus, even when signals of the retinal pigment epithelium boundary 6 are omitted due to a disease such as an exudate, the retinal pigment epithelium boundary 6 can be detected without erroneously detecting the exudate.

In the above description, a single mask region is used for the exudate and blood vessel. However, it is desirable to assign labels to masks for an exudate, a druse, bleeding, a blood vessel, and the like so as to identify their mask regions. For example, a label region for a mask is assured to have the same image size as the projection image and 8 bits per pixel. To respective bits, morbid portions and blood vessels detected from the fundus image and tomogram are assigned in advance. Thus, even when a morbid portion and blood vessel are detected to overlap each other at the same coordinate position, a plurality of labels can be assigned to the same coordinate position. The bit size can be set depending on types to be identified.

In step S445, the quantifying unit 256 quantifies the morbid features extracted by the feature extraction unit 257. For example, as shown in FIG. 10A, when an exudate exists in a retina, the unit 256 calculates the area, volume, and existing position of the detected exudate, the number of exudates, and the like. The unit 256 calculates the exudate area from the fundus image or projection image, and the exudate volume from the tomogram. Furthermore, when the exudate area, volume, and existing position and the number of white spots, which are quantified previously, are available, comparison with the previously quantified data may be made. The quantifying unit 256 need only calculate at least one of the aforementioned numerical value data and the thicknesses, area, and volume of each layer, and can arbitrarily set data to be quantified. If no data can be calculated, a quantifying failure message may be displayed by the display unit 270 in next step S455.

In step S455, the display unit 270 displays the tomogram and fundus image, the detection results of the layers and layer boundaries of the tomogram, the detection results of the morbid portions, the quantification results associated with the layers of the tomogram, and the quantification results of the morbid portions. If previous data are available, the display unit 270 may display the current data in comparison with the previous data.

According to the aforementioned arrangement, when retina layers to be extracted are specified based on morbid portions and features detected from a fundus image, segmentation of layers suited to an input image can be automatically done, thus providing an effect of reducing the load on the user upon segmentation of the retina layers. Since layers are emphasized in consideration of the thicknesses of the retina layers, and the retina layers are segmented in consideration of blood vessels and morbid portions detected from the fundus image or projection image, layer boundaries can be precisely extracted independently of diseases.

A case will be described below wherein a second determination unit 260 is added to an image processing unit 200 in place of the first determination unit 259. In general, it is difficult to judge diseases such as age-related macular degeneration and edema from a fundus image and projection image. Thus, the second determination unit 260 is added to use shape features of a retina tomogram in addition to image features obtained from the fundus image and projection image. Then, the types of layers to be presented to the user can be robustly selected.

FIG. 11 is a block diagram showing the functional arrangement of an image processing apparatus 11. Since the functional arrangement shown in FIG. 11 is the same as that shown in FIG. 1 except for an image processing unit 201, a description thereof will not be given. The image processing unit 201 includes the second determination unit 260 in place of the first determination unit 259 shown in FIG. 2. The second determination unit 260 makes determination based on feature amounts extracted by a feature extraction unit 257 and detection results of layer structures detected by a layer structure detection unit 254, and outputs the determination result to a layer structure modifying unit 255.

The processing sequence of the image processing apparatus 11 will be described below with reference to the flowchart shown in FIG. 12. Note that the processes in steps S1201 to S1206 and in steps S1214 to S1216 are the same as those in steps S301 to S306 and in steps S310 to S312 in FIG. 3. Also, steps S1207, S1212, and S1213 are the same as steps S410, S440, and S450 in FIG. 4A. Hence, a description of these steps will not be repeated.

In step S1208, the layer structure detection unit 254 calculates an inner limiting membrane 1, nerve fiber layer boundary 2, and retinal pigment epithelium boundary 6. Since the layer detection method is the same as that in step S420, a description thereof will not be repeated. Note that when a morbid portion is detected from the fundus image in step S1204, layers may be calculated in a mask region of the morbid portion of the tomogram by interpolation from the detection positions of the layers in the vicinity of a mask region. Then, the layer structure detection unit 254 calculates an inner plexiform layer boundary 3, outer plexiform layer boundary 4, and junction 5 between inner and outer photoreceptor segments. However, since these layers are not detected due to the influence of a disease, it is desirable not to detect these layers or to calculate them by interpolation processing in advance in the mask region of the morbid portion in the tomogram.

In step S1209, the feature extraction unit 257 extracts image features and shape features of retina layers from the tomogram. The image features of the tomogram will be described first. In this case, the feature extraction unit 257 uses the position information of the inner limiting membrane 1 and retinal pigment epithelium boundary 6 detected in step S1208. That is, the feature extraction unit 257 limits a range for extracting image features to that between the inner limiting membrane 1 and retinal pigment epithelium boundary 6. The tomogram of the retina layers has different intensities for respective layers. In case of a normal eye, a nerve fiber layer 2' and photoreceptor layer between the junction 5 between inner and outer photoreceptor segments and the retinal pigment epithelium boundary 6 have high intensities. When an exudate exists inside retina layers, a region of the exudate has high intensities, and the photoreceptor layer between the junction 5 between inner and outer photoreceptor segments and the retinal pigment epithelium boundary 6 has low intensities. When bleeding is spread in the retina layers, the photoreceptor layer between the junction 5 between inner and outer photoreceptor segments and the retinal pigment epithelium boundary 6 has low intensities as its feature. As image features, primary statistical amounts such as a histogram, secondary statistical amounts such as a density co-occurrence matrix, Fourier features, and the like are extracted. Furthermore, a profile feature of intensities along an A-scan is extracted between the inner limiting membrane 1 and retinal pigment epithelium boundary 6. The right views of FIGS. 8A and 10A show the profile of intensities. In addition to these image features, gradient features of an image, and feature amounts of a layer structure-emphasized image by a Hessian matrix may be used.

The shape features of the retina layers will be described below. The inner limiting membrane 1 has an upward convex shape as a feature since blood is accumulated in the retina when the interior of the retina layers has bleeding. The layer shape of the retinal pigment epithelium 6 is deformed to have a concave-convex shape due to a newborn blood vessel formed from its lower portion as a feature when the retinal pigment epithelium 6 suffers age-related macular degeneration. For this reason, the shape feature of the layer can be used as one feature used to identify a morbid portion. The shape feature can be extracted by calculating a curvature of neighboring detection points in a single layer. The image features and shape features from the tomogram may be extracted with or without a limitation to the interior of the mask region extracted from the fundus image and projection image. When only the image features of the tomogram are used, they may be calculated from the entire image without using the positions of layers. Note that the retina layers have different shapes in a macula portion and optic papilla. For example, as a feature, the inner limiting membrane 1 has a downward convex shape at a position near the center of the optic papilla rather than a position near the center of a macula portion. Also, as another feature, when a retina falls to a disease, since an optic papilla fovea is enlarged, the shape of the inner limiting membrane 1 is enlarged. For this reason, learning is made in next step S1210 in consideration of differences of features due to differences of portions.

In step S1210, the second determination unit 260 judges the presence/absence and type of a morbid portion using the image features calculated from the fundus image and the image features and shape features of respective layers calculated from the tomogram, and decides the types of layers to be output to the user. For example, by learning the image features and the shape features of layers calculated from the tomograms in normal and morbid states using an identifier such as a Support Vector Machine or AdaBoost, a morbid portion can be determined.

In step S1211, the layer structure modifying unit 255 modifies the results of the layer structures of all the layers when the second determination unit 260 determines based on the image feature amounts extracted from the fundus image and tomogram that no morbid portion exists. On the other hand, the layer structure modifying unit 255 modifies some layer structures, that is, the result of the retinal pigment epithelium boundary 6 when the second determination unit 260 determines that a morbid portion exists. In this case, the layer structure modifying unit 255 searches for a gradient feature in vertical direction within a given range to have positions of the layers calculated by interpolation by the layer structure detection unit 254 as initial values, thus detecting respective layers.

According to the aforementioned arrangement, the types of layers to be presented to the user are selected using the image features or the shape features of layers obtained from the tomogram of the retina layers in addition to the image features obtained from the fundus image and projection image. Since the feature amounts inside the retina layers are used in addition to those of a surface image of an eye portion, the types of layers to be presented to the user can be robustly selected.

Next, a case will be described below wherein the processing contents of a feature extraction unit 257 and first determination unit 259 are changed. This embodiment is different from the above embodiments in that weights are set for feature amounts extracted by the feature extraction unit 257, and the first determination unit 259 selects feature amounts to be back-projected onto a tomogram as a mask region from those extracted from a fundus image and projection image.

In this embodiment, in place of using all feature amounts extracted from a fundus image and projection image as a mask region at the time of detection of a tomogram, feature amounts having higher likelihoods are selected from those obtained from the tomogram and fundus image and are set as a mask region of the tomogram. More specifically, a mask region is set only on a region where a signal attenuation is more likely to be generated on the tomogram. For this reason, as for a region where a signal attenuation is unlikely to be generated on the tomogram, since a layer is directly detected in place of approximating a layer by interpolation, a layer structure can be detected more precisely.

Figure 3:
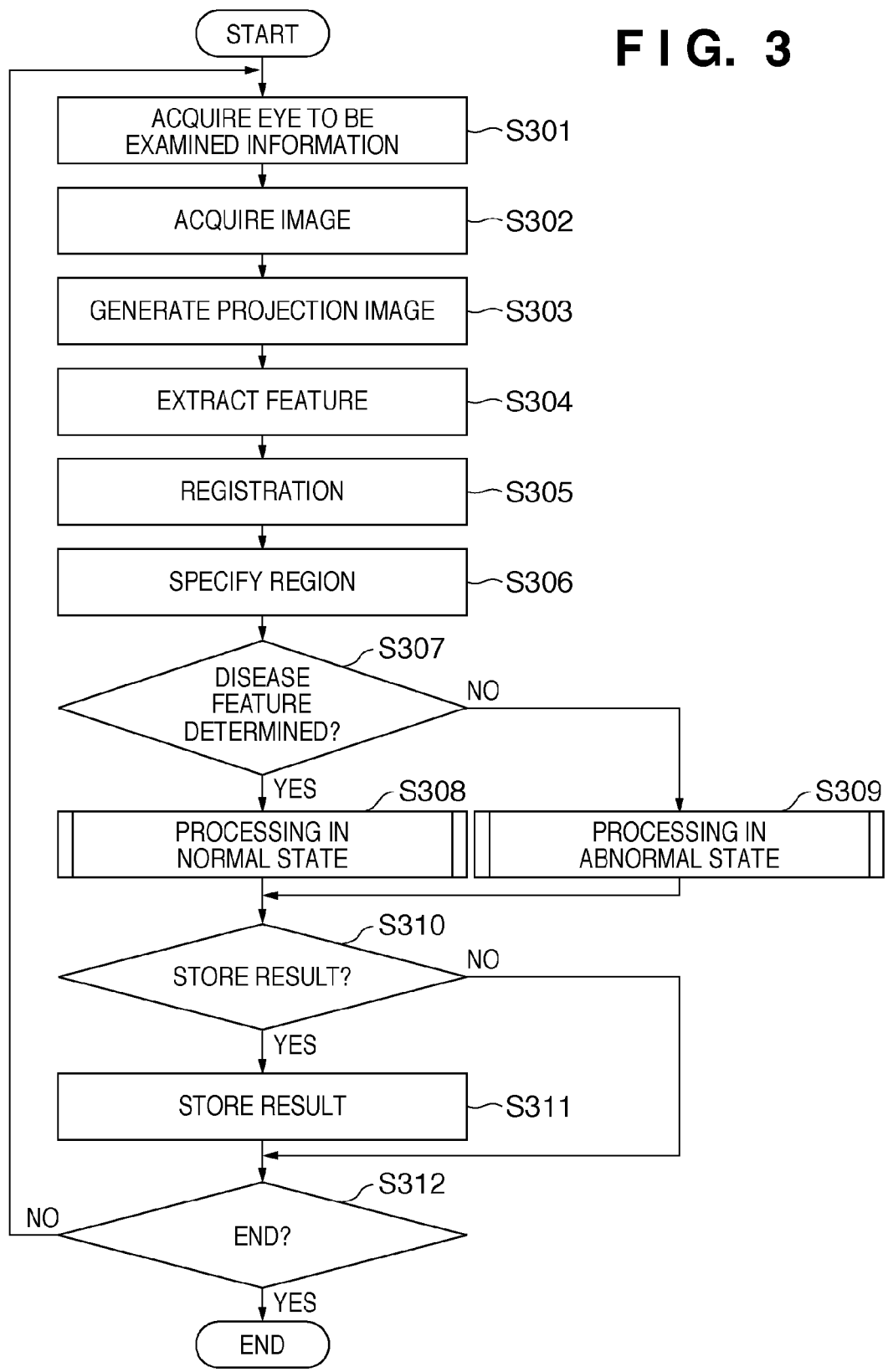
FIG. 3 is a flowchart showing the retina layer structure analysis processing sequence according to the embodiment.

This embodiment is different from the above embodiments in that steps S304 and S307 in FIG. 3 have different processing contents, and region specifying processing in step S306 is executed according to the determination result in step S307. Since other processes are the same as those in the above embodiments, a description thereof will not be repeated. A case will be explained below wherein the feature extraction unit 257 detects a blood vessel. Note that morbid portions (an exudate, druse, bleeding, etc.) other than the blood vessel can be calculated in the same manner as in the following processing.

When the feature extraction unit 257 detects blood vessels from a projection image and fundus image in step S304, it holds output values equal to or larger than a threshold intact without binarizing output results of a blood vessel detection filter via threshold processing. Alternatively, the feature extraction unit 257 may convert a filter output value into multi-values by dividing it into some values within a range from a threshold to a maximum value. Alternatively, the feature extraction unit 257 may multiply a filter output value by a weighting function that assumes 0 for the filter output value equal to or smaller than a threshold and assumes 1 for a maximum value. In this manner, since a feature amount is extracted as a value that reflects an existence likelihood of an anatomical feature, an output value of a region which is likely to be a blood vessel becomes large and an output value of a region near the threshold becomes small in a region detected as the blood vessel by the feature extraction unit 257. Note that when the projection image and fundus image have different numbers of bits per pixel, it is desirable to apply normalization processing to these images.

In step S307, the first determination unit 259 selects regions having high likelihoods as a blood vessel by selecting regions having large filter output values from the projection image and fundus image. Selecting those having feature amounts equal to or larger than a predetermined value can attain the selection method of regions from the projection image and fundus image. In addition, a known identifier may be used, or top several % of regions equal to or larger than a threshold may be determined.

According to the aforementioned arrangement, as for a region where a signal attenuation is unlikely to be generated on a tomogram, since a layer is directly detected without approximating a layer by interpolation, the layer structure can be detected more precisely.

A case will be described below wherein a layer structure update unit is added to an image processing unit 200 shown in FIG. 1. The layer structure update unit serves to update the positions of a layer, which are independently detected for respective A-scans, to have a three-dimensionally smooth layer shape. For this purpose, an image processing apparatus further includes the layer structure update unit between a layer structure modifying unit 255 and quantifying unit 256 in the image processing unit 200 shown in FIG. 1. Other components are the same as those in FIG. 1.

The processes at the time of normal and abnormal processes in the image processing unit of this embodiment are basically the same as those in FIGS. 4A and 4B, except that layer structure detection result update processing is executed after the layer structure detection result modifying processing in steps S430 and S435. The layer structure detection result update processing in the image processing unit of this embodiment will be described below.

The layer structure update unit updates results of retina layers, which are detected by a layer structure detection unit 254 and are modified by the layer structure modifying unit 255. Upon application of an active contour method such as Snakes or a level set method, the layer structure update unit makes iterative calculations to minimize an energy value to have the detection result of the layer structure detection unit 254 as an initial value. In case of Snakes, the layer structure update unit defines an image energy and shape energy, and repeats a calculation to minimize the sum of these energies. An energy formula of Snakes is described by:

$$E = E_{shape\_local} + E_{image} \quad (10)$$

where E is an entire energy value, $E_{shape\_local}$ is a shape energy value, and $E_{image}$ is an image energy value. In this way, an energy value converges to an edge of an image while maintaining a smooth layer structure. The layer structure update unit updates the modification results of the retina layers based on the energy obtained in this way.

For example, the image energy is defined by an intensity gradient at respective detection points and a variance sum of intensities in upper and lower layers, as given by:

$$E_{image} = w_e E_{edge} + w_v (E_{variance\_of\_upper\_layer} + E_{variance\_of\_lower\_layer}) \quad (11)$$

where $E_{edge}$ is an intensity gradient at respective control points, $E_{variance\_of\_upper\_layer}$ is a variance of intensities of an upper layer, and $E_{variance\_of\_lower\_layer}$ is a variance of intensities of a lower layer. $w_e$ and $w_v$ are weights. In this way, since the variances of intensities of the upper and lower layers are defined as image features, an image energy acts to be converged to a layer boundary even at the layer boundary where it is attenuated due to a blood vessel or morbid portion, and an image gradient cannot be obtained. For example, in case of a nerve fiber layer boundary 2, $E_{variance\_of\_upper\_layer}$ minimizes a variance of intensities of a layer (nerve fiber layer 2') between itself and an inner limiting membrane 1. $E_{variance\_of\_lower\_layer}$ minimizes a variance of intensities of a layer (a ganglion cell layer (not shown)+an inner plexiform layer) between the nerve fiber layer boundary 2 and an inner plexiform layer boundary 3. In this embodiment, the lower layer is defined as a layer between the nerve fiber layer boundary 2 and the inner plexiform layer boundary 3. Alternatively, the ganglion cell layer (not shown) may be defined as a lower layer. Note that the image energy defined by equation (11) may have different definitions for respective layers. For example, since the inner limiting membrane 1 is not influenced by a blood vessel or morbid portion, only $E_{edge}$ may be defined.

The shape energy acts to smoothen between respective detection points by defining shape features such as a first differential and second differential. Note that weights to be given to the shape energy and image energy may be changed between a mask region and a region outside the mask region. For example, when a signal attenuation in a mask region is more likely to occur, a weight for the image energy with a low reliability is set to be small, and that for the shape energy is set to be large. By increasing the weight for the shape energy, a smooth layer can be detected.

According to the aforementioned arrangement, layer boundaries can be detected according to the state of a retina. A layer which suffers a signal attenuation due to a blood vessel or a morbid portion such as an exudate is detected, and the detection result is updated to detect a layer boundary while maintaining the layer shape structure. For this reason, the layer structures of the retina can be three-dimensionally smoothly detected.

An arrangement, in which the fundus image acquisition unit 222 is omitted from that shown in FIG. 11 so as to cope with a case in which no fundus image is available and only a tomogram is available, will be described below. Since other components are the same as those in FIG. 11, a description thereof will not be repeated. The processing sequence of the image processing apparatus is substantially the same as that shown in FIG. 12, except that the processes in steps S1205 and S1206 are excluded. Also, another difference from the above embodiments is that input images include only a tomogram, and a projection image generated from the tomogram.

Therefore, in step S1202 a tomogram acquisition unit 221 acquires a tomogram transmitted from a tomography apparatus 20. Then, the unit 221 transmits the acquired information to a storage unit 240. In step S1204, a feature extraction unit 257 extracts blood vessels and morbid portions from a projection image generated by a projection image generation unit 251. The extraction method of these blood vessels and morbid portions is the same as that in step S304. However, an extraction target is the projection image. Also, the feature extraction unit 257 may extract a macula portion, optic papilla, and the like in addition to the blood vessels and morbid portions. These feature amounts may also be used to reduce detection errors in extraction of the blood vessels and morbid portions. In step S1209, the feature extraction unit 257 extracts features of the morbid portions from the tomogram. In this case, the feature extraction unit 257 desirably executes feature extraction processing for entire retina layers in place of the processing in only a mask region in the retina layers.

According to the aforementioned arrangement, when only a tomogram is available, diagnosis information data required to diagnose a plurality of types of diseases can be acquired from a tomogram of an eye portion without increasing the load on the user.

In the aforementioned embodiments of the present invention, the types of layers to be measured are selected using only feature amounts obtained from images. However, when previous examination results are available, layers to be segmented are often decided beforehand. Therefore, using this information, the processing can be simplified or speeded up.

In consideration of this point, the first determination unit 259 or second determination unit 260 according to the above embodiment determines the types of layers to be detected using information acquired by the ETBE information acquisition unit 210. When the ETBE information acquisition unit 210 acquires examination results associated with the eye to be examined, and the examination results include previous examination results associated with the tomography apparatus 20, it acquires information of retina layers measured at the time of immediately preceding tomography. Thus, in case of follow-up, the first determination unit 259 or second determination unit 260 selects the same layers as those of retina layers used in quantification at the time of immediately preceding tomography. Alternatively, when the ETBE information acquisition unit 210 acquires an examination result associated with the eye to be examined, and the examination result describes a case name, it acquires that information. In this way, the first determination unit 259 or second determination unit 260 can select the types of layers to be measured from examination results of an examination apparatus other than the tomography apparatus 20.

According to the aforementioned arrangement, using the ETBE information, the processing can be speeded up, and layers to be extracted can be specified more precisely.

In the aforementioned embodiments, the layer structure emphasizing processing is applied to an entire image. However, it is inefficient to apply the layer structure emphasizing processing to an image region other than retina layers, and a long processing time is required. A case will be described below wherein retina layers are detected and are set as a region of interest prior to the layer structure emphasizing processing, which is applied to only the interior of this region of interest, so as to shorten the time required for the entire layer structure detection processing sequence. In order to speed up the processing, the processes are modified as follows in the respective embodiments. In this case, the following description will be given taking one embodiment as an example. However, when the same processing is applied to other embodiments, the processes of these embodiments can also be speeded up.

The speed-up processing corresponding to this embodiment is basically the same as those in FIGS. 4A and 4B, except that region of interest detection processing is executed before the layer structure emphasizing processing in steps S410 and S415. Other processes are the same as those in FIGS. 4A and 4B. The region of interest detection processing in the image processing unit will be described below.

The layer structure detection unit 254 detects a layer, whose layer structure is easily detected, in advance, and detects the entire region of retina layers as a region of interest with reference to that layer. For example, the unit 254 detects the inner limiting membrane 1, and approximates the detected point group by a multi-dimensional curve. Then, the unit 254 sets a region from there until a given distance in the depth direction as a region of interest. Alternatively, the unit 254 also detects the retinal pigment epithelium boundary 6, and approximates the detected point group by a multi-dimensional curve. Then, the unit 254 sets a region between the inner limiting membrane 1 and retinal pigment epithelium boundary 6 detected by approximation as a region of interest. Alternatively, the unit 254 detects a retina layer region simply by threshold processing, and applies labeling processing to the detected region. Then, the unit 254 sets a region of interest to surround labeling regions with top two numbers of coupled pixels. With these processes, the unit 254 can detect the retina layers as a region of interest.

Then, the layer structure emphasizing processing in step S410 or S415 is applied to the interior of only the region of interest, which is set by the above processing. Also, upon detection of layer structures in step S420 or S425, a search region is limited to the region of interest. Note that even when the region of interest detection processing detects the inner limiting membrane 1 and retinal pigment epithelium boundary 6 in advance, the processing in step S420 or S425 may detect them again using layer structure-emphasized image features.

According to the aforementioned arrangement, the layer structure emphasizing unit 253 applies the layer structure emphasizing processing to the interior of only the region of interest, and the layer structure detection unit 254 sets the interior of only the region of interest as a search region. Therefore, since the processing is executed in only the region of interest, the time required for the entire layer structure detection processing sequence can be shortened.

Other Embodiments

Figure 13:
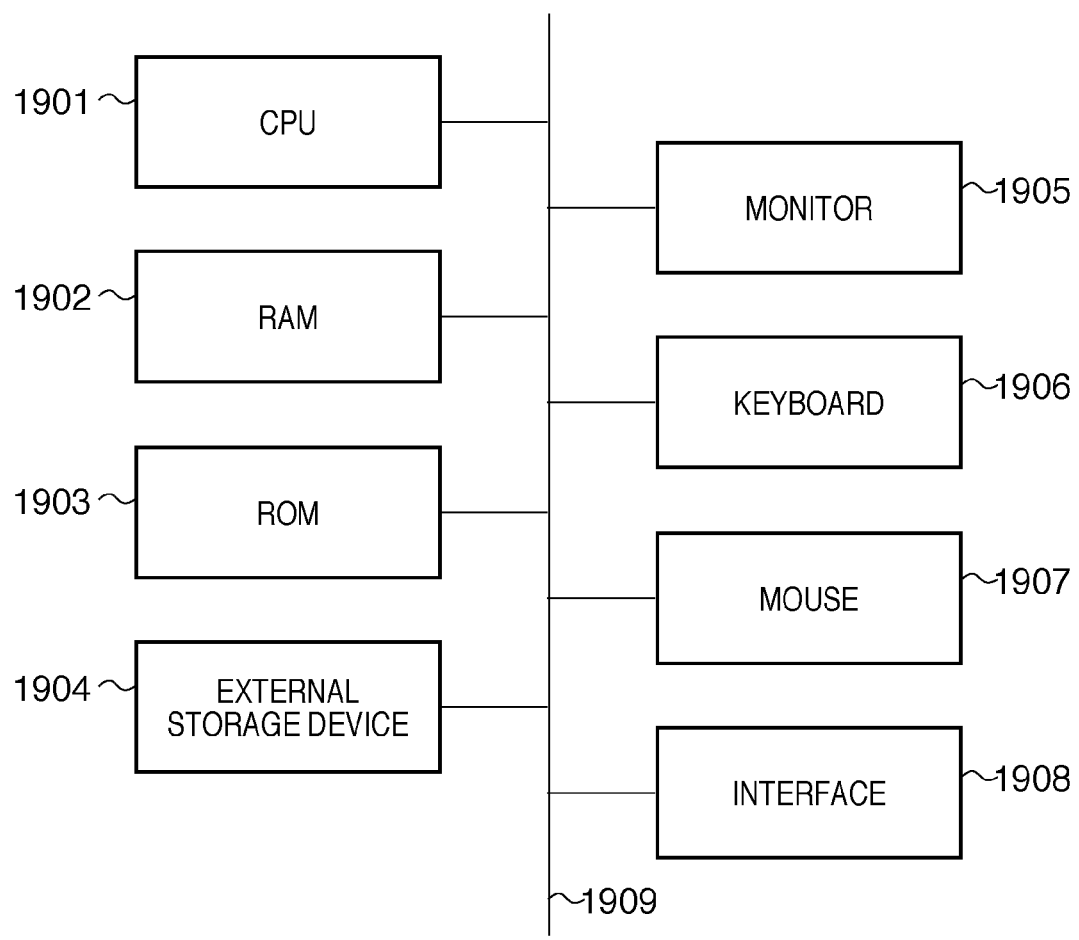
FIG. 13 is a block diagram showing the basic arrangement of an image processing apparatus according to an embodiment.

The aforementioned embodiments implement the present invention as an image processing apparatus. However, an embodiment of the present invention is not limited to only the image processing apparatus. This embodiment implements the present invention as software which runs on a computer. FIG. 13 is a block diagram showing the basic arrangement of a computer used to implement the functions of respective units of an image processing apparatus 10 as software. A CPU 1901 controls the overall computer using programs and data stored in a RAM 1902 and ROM 1903. Also, the CPU 1901 implements the functions of the respective units by controlling execution of software programs corresponding to the respective units of the image processing apparatus 10. The RAM 1902 includes an area for temporarily storing computer programs and data loaded from an external storage device 1904, and also an area required for the CPU 1901 to execute various processes. The function of a storage unit 240 is implemented by the RAM 1902 and the like.

The ROM 1903 generally stores a BIOS, setting data, and the like of the computer. The external storage device 1904 serves as a large-capacity information storage device such as a hard disk drive, and stores an operating system and computer programs executed by the CPU 1901. The external storage device 1904 stores information that is given in the description of this embodiment, and such information is loaded onto the RAM 1902 as needed. A monitor 1905 is configured by, for example, a liquid crystal display. For example, the monitor 1905 can display the contents output from a display unit 270. A keyboard 1906 and mouse 1907 are input devices. An operator can input various instructions to the image processing apparatus 10 using these input devices. The functions of an ETBE information acquisition unit 210 and instruction acquisition unit 230 are implemented via these input devices.

An interface 1908 is used to exchange various data between the image processing apparatus 10 and external apparatuses, and is configured by, for example, an IEEE1394, USB, or Ethernet® port. Data acquired via the interface 1908 is fetched onto the RAM 1902. Functions of an image acquisition unit 220 and result output unit 280 are implemented via the interface 1908. The aforementioned components are interconnected via a bus 1909.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-133454, filed Jun. 2, 2009, which is hereby incorporated by reference herein in its entirety.

The invention claimed is:

1. An image processing apparatus, which analyzes retina layers of an eye to be examined, comprising:
    one or more processors; and
    at least one memory coupled to the one or more processors, the at least one memory having instructions stored thereon which, when executed by the one or more processors, cause the image processing apparatus to:
        extract a feature amount, which represents an anatomical feature in the eye to be examined from a fundus image of the eye to be examined;

detect structures of the retina layers in a tomogram of the retina layers, wherein the tomogram corresponds to the fundus image;

extract information of a shape of at least one retina layer based on the detected structures of the retina layers;

determine whether the anatomical feature includes a first morbid portion or a blood vessel based on the feature amount and to determine whether or not the anatomical feature includes an age-related macular degeneration as a second morbid portion based on the information of the shape;

decide at least one layer including a retinal pigment epithelium layer from the retina layers according to the determination of whether the anatomical feature includes the first morbid portion or the blood vessel; and modify the decided at least one layer and estimate, in a case where the anatomical feature includes the second morbid portion, a normal structure of the retinal pigment epithelium layer.

2. The image processing apparatus according to claim 1, wherein when the anatomical feature includes a blood vessel, a feature amount of the blood vessel is extracted using a filter which emphasizes a linear structure, and wherein a structure of a layer, which neighbors the blood vessel, is modified by limiting a search range by interpolation using a boundary of the layer, which neighbors the blood vessel, and re-detecting a layer structure within the search range.

3. The image processing apparatus according to claim 1, wherein when the anatomical feature includes the first morbid portion, a feature amount of the first morbid portion is extracted based on pixel values, and wherein the decided at least one layer is modified by interpolation using a boundary of the decided at least one layer.

4. The image processing apparatus according to claim 1, wherein the feature amount is extracted as a value which reflects an existence likelihood of the anatomical feature in the eye to be examined, and wherein the decided at least one layer having the likelihood not less than a predetermined value is modified.

5. The image processing apparatus according to claim 1, wherein the at least one memory has further instructions stored thereon which, when executed by the one or more processors, cause the image processing apparatus to update the decided at least one layer which has been modified, wherein an energy value is calculated based on at least one of an image energy based on variances of intensities in layers which sandwich detection points and an intensity gradient at the detection points, and a shape energy that represents a smoothness of a shape of the layer formed by connecting the detection points, and wherein the decided at least one layer is updated based on a specified layer boundary.

6. The image processing apparatus according to claim 1, wherein the feature amount is extracted from the fundus image of the eye to be examined, wherein when the anatomical feature includes a blood vessel, a feature amount of the blood vessel is extracted using a filter that emphasizes a linear structure, and wherein when the anatomical feature includes the first morbid portion, a feature amount of the first morbid portion is extracted based on pixel values.

7. A control method of an image processing apparatus, which analyzes retina layers of an eye to be examined, the control method comprising:

extracting a feature amount, which represents an anatomical feature in the eye to be examined from a fundus image of the eye to be examined;

detecting structures of the retina layers in a tomogram of the retina layers, wherein the tomogram corresponds to the fundus image;

extracting information of a shape of at least one retina layer based on the detected structures of the retina layers;

determining whether the anatomical feature includes a first morbid portion or a blood vessel based on the feature amount and determining whether or not the anatomical feature includes an age-related macular degeneration as a second morbid portion based on the information of the shape;

deciding at least one layer including a retinal pigment epithelium layer from the retina layers according to the determination of whether the anatomical feature includes the first morbid portion or the blood vessel;

modifying the decided at least one layer; and estimating, in a case where the anatomical feature includes the second morbid portion, a normal structure of the retinal pigment epithelium layer.

8. A non-transitory computer readable storage medium storing a computer program for causing a computer to function as an image processing apparatus, which analyzes retina layers of an eye to be examined, to:

extract a feature amount, which represents an anatomical feature in the eye to be examined from a fundus image of the eye to be examined;

detect structures of the retina layers in a tomogram of the retina layers, wherein the tomogram corresponds to the fundus image;

extract information of a shape of at least one retina layer based on the detected structures of the retina layers;

determine whether the anatomical feature includes a first morbid portion or a blood vessel based on the feature amount and to determine whether or not the anatomical feature includes an age-related macular degeneration as a second morbid portion based on the information of the shape;

decide at least one layer including a retinal pigment epithelium layer from the retina layers according to the determination of whether the anatomical feature includes the first morbid portion or the blood vessel; and modify the decided at least one layer and estimate, in a case where the anatomical feature includes the second morbid portion, a normal structure of the retinal pigment epithelium layer.

9. The image processing apparatus according to claim 1, wherein a type of the second morbid portion in the retina layers is further determined.

10. The control method of claim 7, wherein a type of the second morbid portion in the retina layers is determined.

11. The image processing apparatus according to claim 5, wherein detection points that form a detected layer are used to specify a layer boundary which minimizes an energy value.

12. An image processing apparatus comprising:
one or more processors; and
at least one memory coupled to the one or more processors, the at least one memory having instructions stored thereon which, when executed by the one or more processors, cause the image processing apparatus to:

extract a first morbid portion from a fundus image of an eye to be examined;

specify a region in a tomogram of a fundus of the eye to be examined onto which the first morbid portion is projected;

determine whether or not an age-related macular degeneration as a second morbid portion in the tomogram is present based on information of a shape of at least one layer including a retinal pigment epithelium layer of the fundus;

estimate, in a case where the second morbid portion is present, a normal structure of the retinal pigment epithelium layer;

decide at least one layer of the fundus according to the specified region onto which the first morbid portion is projected; and interpolate the decided at least one layer in the tomogram at the specified region onto which the first morbid portion is projected.

13. The image processing apparatus according to claim 12, wherein the region includes an artifact region caused by the first morbid portion.

14. The image processing apparatus according to claim 12, wherein the at least one memory has further instructions stored thereon which, when executed by the one or more processors, cause the image processing apparatus to:

control a display unit to display a display form indicating an interpolated layer; and determine whether or not the first morbid portion exists, wherein, when existence of the first morbid portion is determined, a retinal pigment epithelium layer is interpolated as the at least a layer.

15. The image processing apparatus according to claim 12, wherein at least one of an exudate region and a bleeding region is extracted as the first morbid portion from the fundus image, wherein the exudate region is a region which has signals having higher levels than those around the exudate region, and the bleeding region is a region which has signals having lower levels than those around the bleeding region and is not a blood vessel region having a linear structure, and wherein a layer of a plurality of layers of the tomogram, which is located deeper than a predetermined position corresponding to the first morbid portion, is interpolated.

16. An image processing method using an image processing apparatus which processes a tomogram of a fundus of an eye to be examined and a fundus image of the eye to be examined, the method comprising:

extracting a first morbid portion from the fundus image;

specifying a region in the tomogram onto which the first morbid portion is projected determining whether or not an age-related macular degeneration as a second morbid portion in the tomogram is present based on information of a shape of at least one layer including a retinal pigment epithelium layer of the fundus;

estimating, in a case where the second morbid portion is present, a normal structure of the retinal pigment epithelium layer;

deciding at least one layer of the fundus according to the specified region onto which the first morbid portion is projected; and interpolating the decided at least one layer in the tomogram at the specified region onto which the first morbid portion is projected.

17. A non-transitory computer readable storage medium storing a computer program for causing a computer to function as an image processing apparatus to:

extract a first morbid portion from a fundus image of an eye to be examined;

specify a region in a tomogram of a fundus of the eye to be examined onto which the first morbid portion is projected;

determine whether or not an age-related macular degeneration as a second morbid portion in the tomogram is present based on information of a shape of at least one layer including a retinal pigment epithelium layer of the fundus;

estimate, in a case where the second morbid portion is present, a normal structure of the retinal pigment epithelium layer;

decide at least one layer of the fundus according to the specified region onto which the first morbid portion is projected; and interpolate the decided at least one layer in the tomogram at the specified region onto which the first morbid portion is projected.

18. The image processing apparatus according to claim 1, wherein the number of the decided at least one layer in a region having the first morbid portion is less than the number of the decided at least one layer in a region having the blood vessel.

19. The control method of claim 7, wherein the number of the decided at least one layer in a region having the first morbid portion is less than the number of the decided at least one layer in a region having the blood vessel.

20. The image processing apparatus according to claim 1, wherein, in a case where the anatomical feature includes the blood vessel, layers are decided from the retina layers and, in a case where the anatomical feature includes the first morbid portion, at least one layer is decided from retina layers such that the number of the at least one layer in a region having the first morbid portion is less than the number of the decided layers in a region having the blood vessel.

21. The control method of claim 7, wherein in a case where the anatomical feature includes the blood vessel, layers are decided from the retina layers and in a case where the anatomical feature includes the first morbid portion, at least one layer is decided from retina layers such that the number of the at least one layer in a region having the first morbid portion is less than the number of the decided layers in a region having the blood vessel.

22. An image processing apparatus, which analyzes retina layers of an eye to be examined, comprising:

one or more processors; and at least one memory coupled to the one or more processors, the at least one memory having instructions stored thereon which, when executed by the one or more processors, cause the image processing apparatus to:

extract a feature amount, which represents an anatomical feature in the eye to be examined from a fundus image of the eye to be examined;

detect structures of the retina layers in a tomogram of the retina layers, wherein the tomogram corresponds to the fundus image;

determine whether the anatomical feature includes an age-related macular degeneration or a blood vessel based on the feature amount;

decide at least one layer including a retinal pigment epithelium layer from the retina layers; and modify, in a case where the anatomical feature includes the blood vessel, the decided at least one layer, to estimate, in a case where the anatomical feature includes the age-related macular degeneration, the retinal pigment epithelium layer.

23. A control method of an image processing apparatus, which analyzes retina layers of an eye to be examined, the control method comprising:

extracting a feature amount, which represents an anatomical feature in the eye to be examined from a fundus image of the eye to be examined;

detecting structures of the retina layers in a tomogram of the retina layers, wherein the tomogram corresponds to the fundus image;

determining whether the anatomical feature includes an age-related macular degeneration or a blood vessel based on the feature amount;

deciding at least one layer including a retinal pigment epithelium layer from the retina layers; and modifying, in a case where the anatomical feature includes the blood vessel, the decided at least one layer and estimating, in a case where the anatomical feature includes the age-related macular degeneration, the retinal pigment epithelium layer.

24. A non-transitory computer readable storage medium storing a computer program for causing a computer to function as an image processing apparatus, which analyzes retina layers of an eye to be examined, to:

extract a feature amount, which represents an anatomical feature in the eye to be examined from a fundus image of the eye to be examined;

detect structures of the retina layers in a tomogram of the retina layers, wherein the tomogram corresponds to the fundus image;

whether the anatomical feature includes an age-related macular degeneration or a blood vessel based on the feature amount;

decide at least one layer including a retinal pigment epithelium layer from the retina layers; and modify, in a case where the anatomical feature includes the blood vessel, the decided at least one layer and to estimate, in a case where the anatomical feature includes the age-related macular degeneration, the retinal pigment epithelium layer.

* * * * *